US008148336B2

(12) United States Patent
Shaw et al.

(10) Patent No.: US 8,148,336 B2
(45) Date of Patent: Apr. 3, 2012

(54) STEROL GLUCOSIDE TOXINS

(75) Inventors: Christopher Ariel Shaw, North Vancouver (CA); Raymond J Andersen, Vancouver (CA); David E Williams, Vancouver (CA); Jaswinder Bains, Vancouver (CA)

(73) Assignee: Neurodyn, Inc., Vancouver, British Columbia (CA)

( * ) Notice: Subject to any disclaimer, the term of this patent is extended or adjusted under 35 U.S.C. 154(b) by 1072 days.

(21) Appl. No.: 11/477,730

(22) Filed: Jun. 29, 2006

(65) Prior Publication Data

US 2006/0252705 A1    Nov. 9, 2006

Related U.S. Application Data

(63) Continuation of application No. 10/415,710, filed as application No. PCT/CA01/01567 on Nov. 2, 2001, now abandoned.

(30) Foreign Application Priority Data

Nov. 3, 2000 (CA) .................................... 2325087
Mar. 22, 2001 (CA) .................................... 2342085

(51) Int. Cl.
*C12Q 1/68* (2006.01)
*C12P 19/34* (2006.01)
(52) U.S. Cl. ............................... 514/26; 435/6; 435/7.1
(58) Field of Classification Search .................... None
See application file for complete search history.

(56) References Cited

U.S. PATENT DOCUMENTS

| 4,188,379 A | 2/1980 | Pegel |
| 4,235,992 A | 11/1980 | Ueno et al. |
| 4,254,111 A | 3/1981 | Pegel et al. |
| 4,260,603 A | 4/1981 | Pegel et al. |
| 5,128,324 A | 7/1992 | Walker et al. |
| 5,270,041 A | 12/1993 | Eugster et al. |
| 5,486,510 A | 1/1996 | Bouic et al. |
| 5,753,260 A | 5/1998 | Alving et al. |

FOREIGN PATENT DOCUMENTS

EP    0 858 806    8/1998

OTHER PUBLICATIONS

Khabazian et al.,Journal of Neurochemistry, 2002, vol. 82, p. 516-528.*
Wilson et al. NeuroMolecular Medicine, 2002, vol. 1, p. 207-221.*
Katayama, R., Cheun, M.K., Gorman, L., Tamura, T., and Becker, D.P., "Increase in extracellular glutamate and associated massive ionic fluxes following concussive brain injury," Soc. Neurosci. Abstr., 1998, 14: 1154.
Meister, A. and Tate, S.S., "Glutathione and related gamma glutamyl compounds: biosynthesis and utilization," Annu. Rev. Biochem., 1976, 45: 559-604.

Shaw, C.A. (ed.), Glutathione in the Nervous System, Taylor and Francis Pub., Washington, 1998, pp. 117-136.
Bains, J.S. and Shaw, C.A., "Neurodegenerative disorders in humans: the role of glutathione in oxidative stress-mediated neuronal death," Brain Res. Rev., 1997, 25: 335-358.
Bindokas, V.P., Lee, C.C., Colmers, W.F., and Miller, R.J., "Changes in mitochondrial function resulting from synaptic activity in rat hippocampal slice," J. Neurosci., 1998, 18: 4570-4587.
Bouic and Lamprecht, "Plant Sterols and Sterolins: A Review of Their Immune-Modulating Properties", Altern. Med. Rev., Jun. 1999, 4(3): 170-7.
Bouic et al., "Beta-Sitosterol and Beta-Sitosterol Glucoside Stimulate Human Peripheral Blood Lynphocyte Proliferation: Implications for Their Use as an Immunomodulatory Vitamin Combination", Int. J. Immnopharmacol, Dec. 18, 1996, 18(12): 693-700.
Bouic et al., "The Effects of B-Sitosterol (BSS) and B-Sitosterol Glucoside (BSSG) Mixture on Seleted Immnue Parameters of Maratho Runners: Inhibition of Post Marathon Immune Suppression and Inflammation", Int. J. Sports Med, May 1999, 20(4): 258-262.
Campbell, P.N., Work T.S., and Mellanby, E., "Isolation of crystalline toxic factor from agenized wheat flour," Nature, 1950, 165: 345-346.
Choi, D.W., "Calcium: still center-stage in hypoxic-ischemic neuronal death," Trends Neurosci., 1995, 18: 58-60.
Cooper, A.J.L., "Role of astrocytes in maintaining cerebral glutathione homeostasis and in protecting the brain against xenobiotics and oxidative stress. In: Glutathione in the Nervous System," Shaw, C.A. (ed.), Taylor and Francis Pub., Washington, 1998, pp. 91-116.
Earnshaw, W.C., "Apoptosis: lessons from in vitro systems," Trends Cell Biol., 1995, 5: 217-220.
Ellis R.E., Yuan, J., and Horvitz, H.R., "Mechanisms and functions of cell death," Ann. Rev. Cell Biol., 1991, 7: 663-698.
Evans, P.H., "Free radicals in brain metabolism and pathology," Br. Med. Bull., 1993, 49: 577-587.
Gavreili, Y., Sherman, Y., and Ben-Sasson, S.A., "Identification of programmed cell death via specific labeling of nuclear DNA fragmentation," J. Cell Biol., 1992, 119:493-501.
Gobe, G., "Apoptosis in brain and gut tissue of mice fed a seed preparation of the cycad *Lepidozamia peroffskyana*", Biochemical and Biophysical Research Communications, vol. 205, No. 1, 1994, 327-333, XP002199312.
Goding, "Monoclonal Antibodies: Principles and Practice," 1983, New York Academic Press, pp. 98-118.
Haque, M. et al., "Steryl Glycosides: a Characteristic Feature of the *Helicobacter* spp.," J. Bacteriol., 1995, 177: 5334-5337.
Haque, M. et al. "Lipid Profile of *Helicobacter* ssp: Presence of Cholesteryl Glucoside as a Characteristic Feature", J. Bacteriol., Apr. 1996, 178(7): 2065-2070.

(Continued)

*Primary Examiner* — Yunsoo Kim
(74) *Attorney, Agent, or Firm* — Barnes & Thornburg LLP

(57) ABSTRACT

The invention relates to the identification of sterol glucoside toxins, and provides methods for detecting and detoxifying the compounds, as well as therapeutic methods for treating subjects exposed to such toxins. In alternative embodiments, the toxins may for example include beta-sitosterol-beta-D-glucoside (5-cholesten-24b-ethyl-3b-ol-D-glucoside) or cholesterol glucoside (5-cholesten-3b-ol-3b-D-glucoside).

16 Claims, 12 Drawing Sheets

OTHER PUBLICATIONS

Higuchi, Y. and Matsukawa, S., "Glutathione depletion induces giant DNA and high molecular weight DNA fragmentation associated with apoptosis through lipid peroxidation and protein kinase C activation in C6 glioma cells," Arch. Biochem. Biophys., 1999, 363: 33-42.

Hockenbery, D., Oltvai, Z.N., Yin, X.-M., Millian C.L., and Korsmeyer, S.J., "Bcl-2 functions in an antioxidant pathway to prevent apoptosis," Cell, 1993, 75: 241-251.

Janaky, R., Ogita, K., Pasqualotto, B.A., Bains, J.S., Oja, S.S., Yoneda, Y., and Shaw, C.A., "Glutathione and signal transduction in the mammalian CNS," J. Neurochem., 1999, 73: 889-902.

Kalinowska and Wojciechowski, "Purification and Some Properties of Steryl [Beta}-D-Glucoside Hydrolase From Sinapis Alba Seedlings," Phytochemistry, 1978, 17: 1533-1537.

Kastelic-Suhadolc, T., "Cholesteryl Glucoside in Candida Bogoriensis", Biochim Biophys Acta, Nov. 7, 1980, 620(2): 322-325.

Katayama, R., Cheun, M.K., Gorman, L., Tamura, T., and Becker, D.P., "Increase in extracellular glutamate and associated massive ionic fluxes following concussive brain injury," Soc. Neurosci. Abstr., 1998, 14: 1154.

Khabazian I. et al., "Mechanisms of action of sitosterol glucoside in mammalian CNS", Society for Neroscience Abstracts, vol. 26, No. 1-2, 2000, Abstract No. 771.13, XP001070132.

Khabazian, I., Pelech, S.L., Williams, D.E., Andersen, R.J., Craig, U.-K., Krieger, C., and Shaw, C.A., "Mechanisms of action of sitosterol glucoside in mammalian CNS," Soc. Neurosci. Abstr., 2000, 26: 2074.

Kohler and Milstein, "Continuous cultures of fused cell secreting antibody of predifined specificity", Nature, 1975, 256: 495-497.

Kohler and Milstein, "Derivation of specific antibody-producing tissue culture and tumor lines by cell fusion," Eur. J. Immunol., 1976, 6: 511-519.

Kunimoto, S. et al., "Expression of cholesteryl glucoside by heat shock in human fibroblasts," Cell Stress Chaperones, Jan. 2000, 5(1): 3-7.

Kurland, L.T., "Amyotrophic lateral Sclerosis and Parkinson's disease complex on Guam linked to an environmental toxin," Trends Neurosci., 1988, 11: 51-53.

Lepage, M., "Isolation and characterization of an esterified form of steryl glucoside", J Lipid Res, 1964, 5: 587-592.

Mayberry, W. R. et al., "Structures and Properties of Acyl Diglucosylcholesterol and Galactofuranosyl Diacyglycerol from Acholeplasma Axanthum", Biochim Biophys Acta, 1983, 752: 434-443.

Meister, A. and Tate, S.S., "Glutathione and related gamma glutamyl compounds: biosynthesis and utilization," Annu. Rev. Biochem., 1976, 45: 559-604.

Meldrum, B. and Garthwaite, J., "Excitatory amino acid neurotoxicity and neurodegenerative disease," Trends Pharmacol. Sci., 1990, 11: 379-386.

Nagata, S., "Apoptosis by death factor," Cell, 1997, 88: 355-365.

Newell, G. W., Erickson, T.C., Gilson, W.E., Gerschoff, S.N., and Elvehjem, C.A., "Role of "agenized" flour in the production of running fits," J. Am Med Assoc., 1947, 135: 760-763.

Nicole, A., Santiard-Baron, D., Cellballos-Picot, I., "Direct evidence for GSH as mediator of apoptosis in normal cell death," Biomed. Pharmacother., 1998, 52: 349-355.

Palmer, A.M., "The activity of pentose phosphate pathway is increased in response to oxidative stress in Alzheimer's disease," J. Neural Trans., 1999, 106: 317-328.

Parry et al., "Biochemical characterization and mechanism of action in a thermostable [Beta]-glucosidase purified from *Thermoascus aurantiacus*", Biochem J, Jan. 1, 2001, 353(Pt 1): 117-127.

Perl, T.M., Bedard, L., Kosatsky, T., Hockin, J.C., Todd, E.C.D., and Remis, R.S. An outbreak of toxic encephalopathy caused by eating muscles contaminated with domoic acid. N. Eng. J. Med. 1990, 322: 1775-1780.

Peterson, G.L., "Review of the Folin phenol protein quantification method of Lowry, Rosebrough, Farr and Randall." Anal. Biochem., 1979, 83: 201-220.

Pow, D.V., Barnett, N.L., and Penfold, P., "Are neuronal glutamate transporters relevant in retinal glutamate homeostatis?" Neurochem. Intl., 2000, 37: 191-198.

Rechcigl, M. and Laqueur, G.L., "Carcinogen-mediated alteration of the rate of enzyme synthesis and degradation," Enzym. Biol. Clin. ,1968, 9: 276-286.

Rechcigl, M., "Rates and kinetics of catalase synthesis and destruction in rats fed cycad and cycasin in vivo," Fed. Proc., 1964, 23: 1376-1377.

Rothstein, J.D., Tsai, G., and Kuncl, R.W., Clawson, L., Cornblath, D.R., Drachman, D.B., Pestronk. A., Staunch, B.L., and Coyle, J.T., "Abnormal excitatory amino acid metabolism in amyotrophic lateral sclerosis," Ann. Neurol., 1990, 28: 18-25.

Rothstein, J.D., Martin, L.J., Kuncl, R.W., "Decreased glutamate transport by the brain and spinal cord in amyotrophic lateral sclerosis," N. Eng. J. Med., 1992, 326: 1464-1468.

Rothstein, J.D., Van Kammen, M., Levey, A., Martin, L.J., and Kuncl, R.W., "Selective loss of glial glutamate transporter GLT-1 in amyotrophic later sclerosis," Ann. Neurol., 1995, 38: 73-84.

Russel, R.L., Siedelak, S.L., Raian, A.K., Bautista, J.M., Smith, M.A., and Perry, G., "Increased neuronal glucose-6-phosphate dehydrogenase and sulfhydryl levels indicate reductive compensation to oxidative stress in Alzheimer's disease," Arch. Biochem. Biophys., 1999, 370: 236-239.

Shaw, C. A., et al., "Did consumption of flour treated by the agene process contribute to the incidence of neurological disease?", Med. Hyp., 1998, 51: 477-481.

Shaw, C. et al., "Identification of a novel excitotoxin from cycad seed: Implications for neuronal disorders," Society for Neuroscience Abstracts, vol. 25, No. 1-2, 1999, 1304, XP001070136.

Shaw, C.A., Bains, J.S., Pasqualoto, B.A., Curry, K., "Methionine sulfoximine shows excitotoxic actions in rat cortical slices," Can. J. Physiol. Pharmacol., 1999a, 77: 871-877.

Shaw, C.A., Pasqualotto, B.A., and Curry, K., "Glutathione-induced sodium currents in neocortex," Neuroreport., 1996, 7: 1149-1152.

Shaw, C.A. (ed.), Glutathione in the Nervous System, Taylor and Francis Pub., Washington, 1998, pp. 117-136.

Shaw, P. J. et al., "Glutamate, excitotoxicity and amyotrophic lateral sclerosis", J. Neurol. 1997, 244 (Suppl. 2): S3-S14.

Sies, H. (Ed.), "Oxidative stress: Oxidants and Antioxidants," Academic Press, New York, 1991, xv-xxii.

Simonian, N.A. and Coyle, J.T., "Oxidative stress in neurodegenerative diseases," Ann. Rev. Pharmacol. Toxicol., 1996, 36: 83-106.

Simpson, R.J., Khabazian, I., Williams, D.E., Andersen, R.J., Craig, U., and Shaw, C.A., "Apoptotic and non-apoptotic cell death following MSO and cycad treatments," Soc. Neurosci. Abstr., 2000, 26:261.

Sugawara et al., "Separation and Determination of Glycolipids from Edible Plant Sources by High Performance Liquid Chromatography and Evaporative Light-Scattering Detection", Lipids, 1999, 34: 1231-1237.

Triosh, O., Sen, C.K., Roy, S., Packer, L., "Cellular and mitochondrial changes in glutamate-induced HT4 neuronal cell death," Neurosci., 2000, 97: 537-541.

Van Huizen, F., Shaw, C., Wilkinson, M., and Cynader, M., "Characterization of muscarinic acetylcholine receptors in rat cerebral cortex slices with concomitant morphological and physiological assessment of tissue viability," Mol. Brain Res., 1989, 5: 59-69.

Verarucci, D., Verarucci, V., Vallese, A., Battila, L., Casado, A., De la Torre, R., and Lopez Fernandez, M.E., "Free radicals: important cause of pathologies refer to aging," Panmineva Medica., 1999, 41: 335-339.

Watanabe, M., "Developmental regulation of ionotropic glutamate receptor gene expression and functional correlations. In: Receptor Dynamics in Neural Development," Shaw, C.A. (e.d.), CRC Press, Boca Raton, 1996, pp. 73-89.

Wullner, U., Seyfried, J., Groscurth, P., Beimroth, S., Winter, S., Gleichmann, M., Heneke, M., Loschmann, P., Schutz, J.B., Weller, M., and Klockgether, T., "Glutathione depletion and neuronal cell death the role of reactive oxygen intermediates and mitochondrial function," Brain Res., 1999, 826: 52-63.

Zaman, K. and Ratan R.R., "Glutathione and the regulation of apoptosis in the nervous system," Glutathion in the Nervous System, Shaw, C.A. (ed.), Taylor and Francis Pub., Washington, 1998, pp. 117-136.

Zeevalk, G.D. and Nicklaus, W.J., "Mechanisms underlying initiation of excitotoxicity associated with metabolic inhibition," J. Pharm. Exp. Ther., 1990, 257: 870-878.

Osborne R. et al., "The magical and medicinal usage of *Stangeria eriopus* in South Africa", Journal of Ethnopharmacology, vol. 43, 1994, 67-72, XP001069718.

Hodgson, et al., "A YAC mouse model for Huntington's Disease with full-length mutant huntingtin, cytoplasmic toxicity, and selective striatal neurodegeneration," Neuron, 1999, 23: 181-192.

Leonard T. Kurland, "Amyotrophic lateral sclerosis and Parkinson's disease complex on Guam linked to an environmental neurotoxin", TINS, vol. 11, No. 2, 1988, pp. 51-54.

\* cited by examiner

STEROL GLUCOSIDE TOXINS

CROSS REFERENCE TO RELATED APPLICATIONS

This application is a continuation of U.S. application Ser. No. 10/415,710, filed Sep. 3, 2003, now abandoned which is a U.S. national application under 35 U.S.C. §371 of PCT Application Serial No. PCT/CA01/01567, filed on Nov. 2, 2001, which claims priority to Canadian Patent Application Serial No. 2,342,085, filed on Mar. 22, 2001, and Canadian Patent Application Serial No. 2,325,087, filed on Nov. 3, 2000.

FIELD OF THE INVENTION

The invention relates to the identification of sterol glucoside toxins, and provides methods for detecting and detoxifying the compounds, as well as therapeutic methods for treating subjects exposed to such toxins.

BACKGROUND OF THE INVENTION

Sterols are a diverse group of lipids, many of which are found in appreciable quantities in animal and vegetal tissues. Sterols may include one or more of a variety of molecules belonging to C27-C30 crystalline alcohols, having a common general structure based on the cyclopentanoperhydrophenanthrene ring (also called sterane). In the tissues of vertebrates, the main sterol is the C27 alcohol cholesterol. There are a variety of other naturally-occurring animal sterols, such as lanosterol (a C30 compound) and 7-dehydrocholesterol, which are illustrative of the structural similarities of sterols. The nomenclature of sterols is based on the numbering of the carbons as exemplified below for cholesterol:

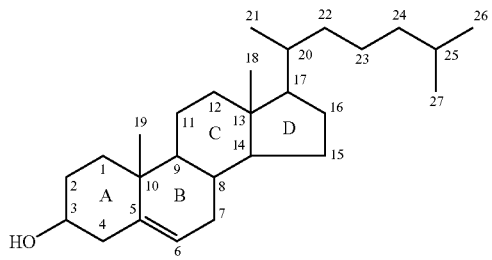

Sterols are also found in plants. The denomination "phytosterol" has been used for sterols of vegetal origin. Chemically, plant sterols generally have the same basic structure as cholesterol, with differences occurring for example in the lateral chain on carbon 17. Cholesterol may itself be found in plants. Representative phytosterols are compounds having 29 or 30 carbon atoms, such as campesterol, stigmasterol and beta-sitosterol (stigmasta-5-en-3beta-ol).

Steryl glycosides are sterol derivatives in which a carbohydrate unit is linked to the hydroxyl group of a sterol molecule. In plants, steryl glycosides have been found in which the sterol moiety is composed of various sterols: campesterol, stigmasterol, sitosterol, brassicasterol and dihydrositosterol. Similarly, the carbohydrate moiety may be composed of a variety of sugars, such as glucose, xylose or arabinose. Sterol glycosides may be obtained from biological sources such as plant tissues by a variety of methods (see for example Sugawara et al. Lipids 1999, 34, 1231; Ueno, et al. U.S. Pat. No. 4,235,992 issued Nov. 25, 1980). An exemplary plant sterol glycoside is beta-sitosterol-beta-D-glucoside (5-cholesten-24b-ethyl-3b-ol-D-glucoside), for which the formula is give below (also showing the structure of the acylated compound):

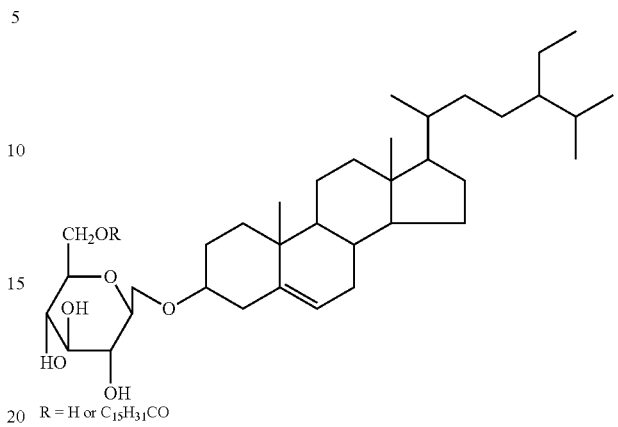

R = H or $C_{15}H_{31}CO$

Acylated sterol glycosides may be formed in plants when a fatty acid is acylated at the primary alcohol group of the carbohydrate unit (such as glucose or galactose) in the steryl glycoside molecule (see Lepage, J Lipid Res 1964, 5, 587). For example, the 6'-palmitoyl-beta-D-glucoside of beta-sitosterol is reportedly present in potato tubers and the 6'-linoleoyl-beta-D-glucoside of beta-sitosterol is reportedly found in soybean extracts. Acylated steryl glucoside may be present at relatively high concentrations in a variety of vegetable parts, with the acylated form being generally more abundant that the non acylated sterol glycoside itself (Sugawara et al., Lipids 1999, 34, 1231).

Sterol glycosides also occur in bacteria. *Helicobacter* has for example been described as being particularly rich in cholesterol glucosides (Haque et al., J. Bacteriol 1995, 177: 5334; Haque et al., April 1996, J Bacteriol; 178(7):2065-70). A cholesterol diglucoside has been reported to occur in *Acholeplasma axanthum* (Mayberry et al., Biochim Biophys Acta 1983, 752, 434).

Sterols and sterol glycosides have been reported to have a wide spectrum of biological activities in animals and humans (Pegel, et al., U.S. Pat. No. 4,254,111 issued Mar. 3, 1981; Pegel et al., U.S. Pat. No. 4,260,603 issued Apr. 7, 1981) and techniques for transdermal administration of these compounds have been suggested (Walker, et al. U.S. Pat. No. 5,128,324 issued Jul. 7, 1992). It has been suggested that some plant sterols, their fatty acid esters and glucosides may be useful for treating cancers (Eugster, et al., U.S. Pat. No. 5,270,041, Dec. 14, 1993). There have been indications that sterols and sterol glycosides are generally non-toxic, or toxic only at relatively high doses while being beneficial at lower doses (Pegel, U.S. Pat. No. 4,188,379 issued Feb. 12, 1980). Some phytosterols are thought to have therapeutic effects, such as anti-tumor properties. Beta-sitosterol is categorized in the Merk Index, Tenth Edition, as an antihyperlipoproteinemic. It has been suggested that beta-sitosterol (BSS), and its glucoside (BSSG) enhance the in vitro proliferative response of T-cells (Bouic et al., Int J Immunopharmacol 1996 December; 18(12):693-700), may have other stimulatory effects as immunomodulators (Bouic et al., Int J Sports Med 1999 May; 20(4):258-62), and may therefore be therapeutically beneficial in a wide variety of diseases because of these immunostimulatory properties (Bouic and Lamprecht, *Altern Med Rev* 1999 June; 4(3):170-7; Bouic et al., U.S. Pat. No. 5,486,510, Jan. 23, 1996).

Cholesterol glucoside (5-cholesten-3b-ol-3b-D-glucoside) is reportedly made by human cells in culture in conjunction with a heat shock response (Kunimoto et al., an 2000, Cell Stress Chaperones; 5(1):3-7). Cholesteryl glucoside has also been reported to occur in *Candida bogoriensis* (Kastelic-Suhadolc, Biochim Biophys Acta 1980 Nov. 7; 620(2):322-5).

Sterol glucosides may be hydrolyzed in acid, such as in methanolic HCl (Kastelic-Suhadolc, Biochim Biophys Acta 1980 Nov. 7; 620(2):322-5). Enzymatic cleavage of the beta-glycosidic linkage may also be accomplished, for example by a beta-d-glucosidase. A thermostable beta-d-glucosidase from *Thermoascus aurantiacus* that hydrolysed aryl and alkyl beta-d-glucosides has for example recently been reported (Parry et al., 1 Jan. 2001, Biochem J, 353 (Pt 1):117-127). A steryl-beta-glucosidase (EC 3.2.1.104; CAS Registration No. 69494-88-8; cholesteryl-beta-D-glucoside glucohydrolase) has been identified from *Sinapis alba* seedlings that reportedly acts on glucosides of cholesterol and sitosterol, but not on some related sterols such as coprostanol, to hydrolyse the glucoside—producing sterol and D-glucose (Kalinowska and Wojciechowski, 1978, Phytochemistry 17: 1533-1537).

Selective neuronal cell death is the common hallmark of various neurodegenerative disorders. At least two mechanisms of neuronal death have been identified within the mammalian central nervous system: necrosis and apoptosis. Necrosis is generally characterized as a passive form of 'accidental' cell death that follows physical damage and is distinguished by membrane permeability changes leading to swelling of cell organelles and rupture of the plasma membrane (Simonian and Coyle, 1996). In contrast, apoptosis is generally characterized as an active form of programmed cell death involving individual cells that often remain surrounded by healthy neighbors. Apoptosis reportedly requires ATP and protein synthesis (Earnshaw, 1995) and has been characterized by cell shrinkage, membrane blebbing, and genomic fragmentation (Ellis et al., 1991; Nagata, 1997).

Both necrosis and apoptosis may be induced by stimulation of neurons by glutamate agonists acting through various glutamatergic excitatory amino acid (EAA) receptor subtypes (Choi, 1995). The actions of glutamate have been classified as either "excitotoxicity" or "excitotoxicity-independent". Excitotoxicity is thought to involve the over-activation of target EAA receptors leading to increased ionic flux. Two main types of excitotoxicity have been described: (1) chronic/slow excitotoxicity, which is thought to result from defects in energy metabolism leading to persistent receptor activation by ambient glutamate (Zeevalk and Nicklas, 1990); and, (2) acute/fast excitotoxicity, which is thought to occur following exposure to high levels of glutamate or glutamate agonists. For example, the over-stimulation of NMDA receptors by glutamate or NMDA may result in increased calcium flux, which in turn may lead to activation of cellular proteases and the activation of other potentially harmful molecules or pathways. It has been suggested that such actions may underlie the damage caused by ischaemia and hypoxia (Choi, 1995; Meldrum and Garthwaite, 1990) or head trauma (Katayama et al., 1988).

Excitotoxicity-independent mechanisms of cell death have been shown to arise due to the accumulation of reactive oxygen species (ROS), elevation of calcium, and the loss of intracellular glutathione (GSH) (Tirosh et al., 2000). Each of these events may induce oxidative stress, described as an imbalance between oxidants (ROS) and antioxidants (GSH, GSH peroxidase, vitamins C and E, catalase, SOD, etc.) with the oxidants becoming dominant (Sies, 1991). Oxidative stress may trigger cellular necrosis (Wullner et al., 1999) as well as apoptosis (Zaman and Ratan, 1998; Hockenbery et al., 1993; Higuchi and Matsukawa, 1999; Nicole et al. 1998) and often arises due to factors leading to GSH depletion. For a number of reasons, neurons are thought to be particularly susceptible to oxidative stress, and oxidative stress-induced cell death has figured in a number of hypotheses concerning neurodegenerative diseases (see Evans, 1993; Simonian and Coyle, 1996; Palmer, 1999; Russel et al., 1999) and aging (Verarucci et al., 1999).

Toxins present in the environment may play a role in human pathology. For example, agenized wheat flour was the most common source of processed flour in much of the Western world for the first fifty years of the $20^{th}$ Century (see Shaw and Bains, 1998; Campbell et al., 1950) and was later found to contain methionine sulfoximine (MSO) in high concentration. MSO induced epileptic seizures in experimental animals ((Newell et al., 1947), an action that was not understood but thought to arise due to MSO acting to inhibit the synthesis of both GSH and glutamine (Meister and Tate, 1976). Subsequent studies have revealed that MSO also has neuro-excitotoxic actions, apparently via NMDA receptor activation (Shaw et al., 1999).

The etiology of various age-related neurological diseases remains largely unknown. Sporadic forms of Alzheimer's, Parkinson's, and Lou Gehrig's disease (amyotrophic lateral sclerosis, ALS) have been linked to environmental factors that cause neuronal cell death by either by excitotoxicity or by inducing oxidative stress. The experimental and clinical literature has been taken to support a potential role for excitotoxins in some forms of neurodegeneration, notably Lou Gehrig's disease and Alzheimer's disease. In particular, abnormalities in glutamate handling/transport have been linked to ALS (Rothstein et al., 1990, 1992, 1995) and domoic acid, a kainate receptor agonist, has been shown to be causal to memory losses much like those reported in Alzheimer's disease (Perl et al., 1990). Oxidative stress has also been linked to the same diseases, particularly following GSH depletion (see Bains and Shaw, 1997). Excitotoxicity and oxidative stress may in fact be innately linked in that neural excitation, particularly over-excitation which occurs in excitoxicity, may generate free radicals acting to increased oxidative stress (Bindokas et al., 1998).

The following abbreviations may be used in the present application: ALS, amyotrophic lateral sclerosis; ALS-PDC, ALS-parkinsonism dementia complex; AMPA, α-amino-3-hydroxy-5-methyl-4-isoxazolepropionic acid; ATP, adenosine triphosphate; BSSG, β-sitosterol-β-D-glucoside; EAA, excitatory amino acid; GluR, glutamate receptor; GSH, glutathione; LDH, lactate dehydrogenase; MSO, methionine sulfoximine; NMDA, N-methyl-D-aspartate; ROS, reactive oxygen species; SOD, superoxide dismutase.

SUMMARY OF THE INVENTION

In one aspect, the present invention discloses the neuronal excitotoxicicity of sterol glycosides. In alternative embodiments, sterol glycosides that are characterized by neuronal excitotoxicity are β-sitosterol-β-D-glucoside (BSSG) and cholesterol glucoside.

In one aspect of the invention, BSSG is identified as a toxin present in the seed of the cycad palm (*Cycas circinalis*), historically a staple of the diet of the Chamorro people of Guam. Cycad seed consumption has been linked to ALS-parkinsonism dementia complex (ALS-PDC), an endemic neurological disorder of Guam (Kurland, 1988). Accordingly, in various embodiments, the present invention provides methods of treating foods to reduce the concentration of sterol glycosides such as BSSG or cholesterol glucoside in foods. In some embodiments, the foods to be treated may for example include plant materials.

An alternative aspect of the present invention is the demonstration that mice fed cycad flour containing BSSG have severe behavioral abnormalities of motor and cognitive function, as well as significant levels of neurodegeneration in the cortex, hippocampus, spinal cord, substantia nigra and other CNS regions measured post mortem. Accordingly, in one aspect the present invention provides an animal model for studying neurodegenerative disease, in which a non-human mammal is fed an excitatory neurotixic sterol glycoside such as BSSG or cholesterol glucoside.

In one aspect, the present invention demonstrates that BSSG may mediate neuronal glutamate release followed by NMDA receptor activation. Accordingly, in one aspect the present invention provides in vitro assays for modulators of cytotoxic action, such as assays for identifying compounds that interfere with cytotoxic neuronal glutamate release mediated by BSSG or cholesterol glucoside. Lactate dehydrogenase assays may for example be used to assay cell death in vitro in conjunction with administration of BSSG and putative inhibitors of cytotoxicity.

In an alternative aspect, the invention provides kits for detecting BSSG or cholesterol glucoside, for example to detect BSSG or cholesterol glucoside in foods or in body fluids. Such kits may for example include immunoassays. In one aspect, the invention accordingly provides antibodies, or other ligands, that bind to the toxins of the invention.

In further alternative aspects, the invention provides methods for treating subjects exposed to the toxins of the invention. For example, such methods may include vaccination with an antigenic composition effective to raise antibodies to the toxins, or treatment of body fluids with an adsorbent, such as an immunoadsorbent, to remove toxins of the invention.

DETAILED DESCRIPTION OF THE INVENTION

Figure 1:
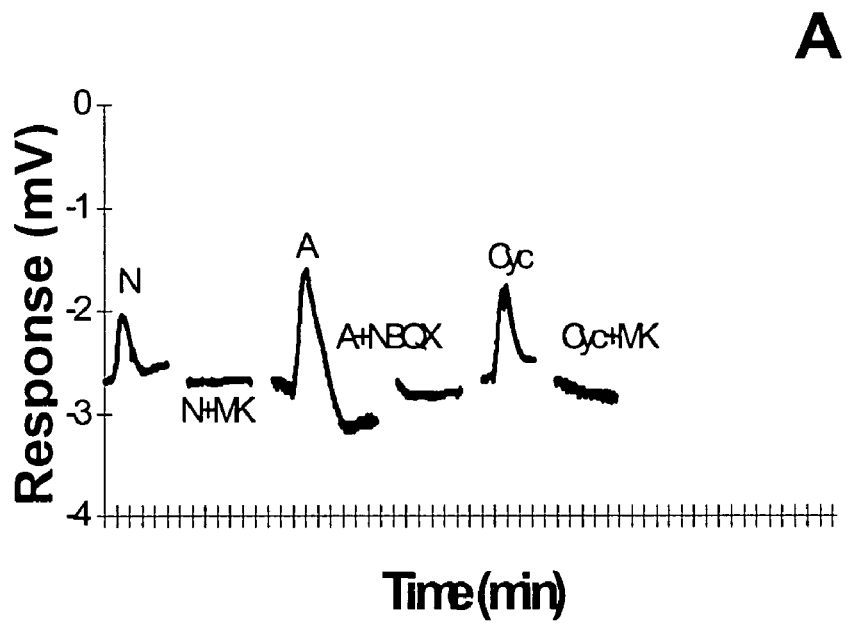
FIG. 1. Shows neuro-excitotoxic action of cycad extract (7× washed cycad chips) demonstrated by in vitro indices of cycad-induced neural activity and toxicity on rat cortical slices. A. Cortical wedge recording of adult rat neocortex. Drugs were administered to the medium bathing each wedge by gravity flow and neural activity differentially recorded as a field potential. MK801 (MK) blocked the NMDA and cycad-induced depolarizations as did AP5 (not shown); NBQX blocked only the AMPA response, but had no effect on the cycad response (not shown). B. Cortical slice assays for LDH release following exposure to various compounds. Cycad fractions in the same concentration as applied to induce depolarization gave greater LDH release than that evoked by NMDA. The effects of both were attenuated by AP5. $Mg^{2+}$ diminished LDH release while freeze-thawing slices maximized cell death. *$P<0.05$, Student's t test. Drug concentrations: NMDA (N), 20 µM; AMPA (A), 10 µM; cycad: 1:50 dilution of crude extract of washed cycad in Krebs-Heinseleit buffer (Cyc).
Figure 1:
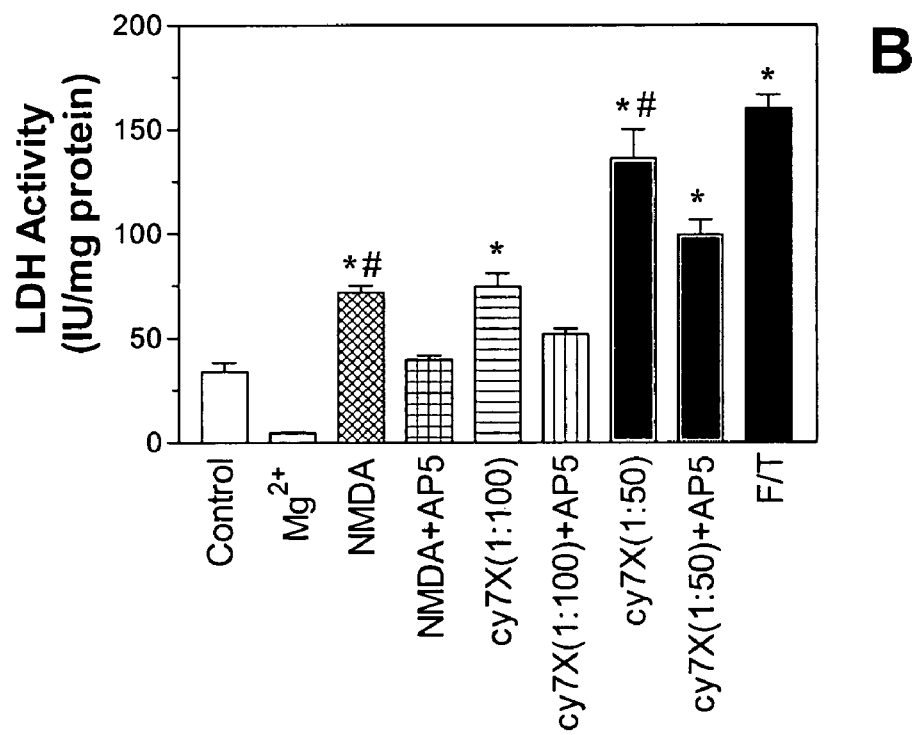

Kits and assays of the invention may include a variety of techniques for detecting toxins. For example, antibodies to BSSG or cholesterol glucoside may be used in kits or assays. Antibodies, or other ligands, that bind to the toxins of the invention may for example be used to prepare kits such as immunoassay agglutination kits designed to detect the toxins in biological specimens, such as blood or feces. Affinity purified antibodies against toxins of the invention may for example be used to passively coat small particles, such as polystyrene particles, that form visible aggregates when they are mixed with a sample containing the toxins. Many alternative immunoassay procedures for detecting toxins of the invention in body fluids may be adapted from methods known in the immunoassay art. Such techniques may include radio-immunoassay techniques; and, enzyme-immunoassay techniques such as competitive, double antibody solid phase ("DASP") and sandwich procedures. Various solid phase immunoassays may be performed using various solid supports, including finely divided cellulose, solid beads or discs, polystyrene tubes and microtiter plates. Enzyme immunoassays may be adapted to include color formation as an indicator of a result.

Procedures for raising polyclonal antibodies are also well known. Typically, such antibodies can be raised by administering an antigenic formulation of the toxin of the present invention subcutaneously to an antibody producing animal, such as New Zealand white rabbits. The antigens may for example be injected at a total volume of 100 microliters per site at six different sites. Each injected material may contain adjuvants. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, Antibodies: A Laboratory Manual (1988), which is hereby incorporated by reference. U.S. Pat. No. 5,753,260 issued to Alving, et al. May 19, 1998 (incorporated herein by reference) discloses immunoreactive compositions and methods for immunizing animals to produce antibodies against sterols, which may be used to produce anti-BSSG or anti-cholesterol glucoside antibodies. Antigenic compositions for raising such antibodies may for example include liposomes containing phosphatidylcholine, toxin (such as BSSG or cholesterol glucoside), and adjuvant such as lipid A in molar ratios of approximately 2:5:0.02. Delivery vehicles other than liposomes would also be suitable, including microcapsules, microspheres, lipospheres, polymers, and slow release devices could serve instead of liposomes.

Monoclonal antibody production to toxins of the present invention may similarly be effected by known techniques involving first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is effected by standard and well-known techniques, for example, by using polyethylene glycol ("PEG") or other fusing agents (see Milstein and Kohler, Eur. J. Immunol. 6:511 (1976), which is hereby incorporated by reference). The resulting fused cells, or hybridomas, are cultured, and the resulting colonies screened for the production of the desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, Nature 256:495 (1975), which is hereby incorporated by reference.

In addition to utilizing whole antibodies, the kits and processes of the present invention encompass use of binding portions of such antibodies that recognize toxins of the invention. Such binding portions include Fab fragments, $F(ab')_2$ fragments, and Fv fragments. These antibody fragments can be made by conventional procedures, such as proteolytic fragmentation procedures, as described in Goding, Monoclonal Antibodies: Principles and Practice, pp. 98-118, New York: Academic Press (1983), which is hereby incorporated by reference.

In one aspect of the invention, ligands (such as antibodies) to the toxins of the invention may be administered to a patient in need of such treatment to ameliorate the effect of the toxins on the patient. In an alternative aspect of the invention, an animal, such as a human, may be vaccinated with an antigenic composition effective to raise antibodies against sterol glucoside toxins of the invention, such as BSSG or cholesterol glucoside, to retard or reduce the severity of toxicity caused by ingestion of toxins of the invention.

In alternative embodiments, the invention provides methods of detoxification of compositions containing toxins, such as foodstuffs, in which sterol glucoside toxins of the invention may be hydrolyzed, for example in acid, such as in methanolic HCl (Kastelic-Suhadolc, Biochim Biophys Acta 1980 Nov. 7; 620(2):322-5). Detoxification by enzymatic cleavage of the beta-glycosidic linkage may also be accomplished, for example by a beta-d-glucosidase. A thermostable beta-d-glucosidase from *Thermoascus aurantiacus* that hydrolyses aryl and alkyl beta-d-glucosides has for example recently been reported (Parry et al., 1 Jan. 2001, Biochem J, 353 (Pt 1):117-127). A steryl-beta-glucosidase (EC 3.2.1.104; CAS Registration No. 69494-88-8; cholesteryl-beta-D-glucoside glucohydrolase) has been identified from *Sinapis alba* seedlings that reportedly acts on glucosides of cholesterol and sitosterol (Kalinowska and Wojciechowski, 1978, Phytochemistry 17: 1533-1537).

In one aspect, the invention provides methods for treatment of materials, such as body fluids, with an adsorbent, such as an immunoadsorbent, to remove toxins of the invention. In such methods, an antibody in an insoluble form may be used to bind the toxin antigen to remove it from a mixture of substances. For example, solid-phase immunoadsorbent gels may be used, in which purified antibodies, for example from the serum of immunized animals, is coupled to cyanogen bromide-activated 4% agarose gels. In alternative embodiments, sephadex, derivatives of cellulose, or other polymers can be used as the matrix as an alternative to agarose.

Alternative aspects of the invention are illustrated in the following Examples, which are merely illustrative of some embodiments and do not necessarily reflect the full scope of the invention.

EXAMPLES

Animals

In vitro experiments were performed on adult (>70 do) male Sprague-Dawley colony rats maintained on a light-dark cycle (12 hr:12 hr). In vivo experiments were conduced using CD-1 colony reared 5-7 mo. old male mice.

Chemicals

MSO was obtained from Sigma-Aldrich Canada Ltd. (Mississauga, Ontario). AMPA, NMDA, AP5, and NBQX were obtained from Precision Biochemicals Inc. (Vancouver, British Columbia). [$^3$H] CGP 39653 and [$^3$H] glutamate were purchased from NEN/Mendel Scientific Co. (Guelph, Ontario). LDH kits and DNAase were obtained from Sigma (St. Louis). TUNEL kits were purchased from Intergen (ApopTag). (Oxford). Other chemicals were of analytical grade available from BDH Inc. (Vancouver, British Columbia).

Cycad Extracts and Purification of BSSG Initial experiments were performed with crude cycad flour extracts made by extensively grinding chips of cycad in a small volume of distilled water. These cycad chips had been extensively soaked over a period of 7 days. This cycad extract was diluted by various factors in Krebs-Henseleit buffer for use in bath application to field potential or LDH assays. Based on early experiments (e.g., see FIG. 2), cycad fractions were extensively screened for potency based on the size of the evoked field potential response or on amount of LDH released. From each stage, the most potent batch was selected and further separated by column chromatography. The fractions ultimately yielded several variants of a sterol glucoside, β-sitosterol-β-D glucoside (BSSG) with a range of molecular weights ranging from 574-576). These fractions have been given fraction identification codes indicating stage in the isolation procedure and are described in the following as D-2, D-1-1, and D-2.

Electrophysiology: Field Potential Recordings

Cortical 'wedges' were prepared as described previously (Shaw et al., 1996). In brief, animals were anesthetized with $CO_2$, decapitated, and a cortical block rapidly removed and placed in cold Krebs-Henseleit buffer containing (in mM): NaCl 124, KCl 3.3, $NaHCO_3$ 25, glucose 10, $KH_2PO_4$ 1.2, $CaCl_2$ 2.4, and $MgSO_4$ 1.2, bubbled with 5% $CO_2$/95% $O_2$, pH 7.4. The cortical block was sectioned into 500 µM thick coronal slices using a Vibratome (Campden Instruments) and the slices cut into pie shaped wedges in which the white matter formed the narrow edge of the wedge. Each wedge was placed on a net across a grease gap between two fluid filled chambers. The cortical side of the wedge was bathed (at room temperature, approx. 25° C.) in buffer lacking $Mg^{2+}$; the callosal portion was bathed in buffer containing $Mg^{2+}$ to minimize neural activity. Field potentials were differentially recorded between the two chambers using two Ag/AgCl electrodes. Recordings from up to 6 wedges, each in individual chambers, could be made simultaneously for each experiment. The wedges were continuously perfused on the cortical side with oxygenated, $Mg^{2+}$-free buffer using a gravity feed system. Using this system, drugs could be rapidly substituted for control media to examine response characteristics. Wedges typically survived for up to 8 hrs. Responses were recorded on LabView™ after amplification and A/D conversion and the traces charted in Excel™ for Windows™. Statistical analysis of peak response amplitude was performed by one-way ANOVA using Bonferroni's post test with GraphPad Prism™.

[$^3$H]-Glutamate Release Studies

Brain slices were taken from cortical blocks in which all subcortical tissue had been removed. 400 µM slices were cut using a modified slice cutter (Van Huizen et al., 1989). Slices were rinsed twice for 5 min in $Mg^{+2}$ containing Krebs-Henseleit buffer pH 7.4. Incubation media consisted of 100 µM cold glutamate, 20 µM AP5 and 10 µM DNQX, the latter NMDA or AMPA antagonists, respectively. 10 nM of [$^3$H]-glutamate was added to the mixture and incubated for 1 hr at 37° C. under in oxygenated atmosphere ($O_2$/$CO_2$=95/5%). Experimental treatments were performed in 500 µM $Mg^{+2}$ free buffer placed in tissue culture wells containing different concentrations of MSO or isolated BSSG fractions of cycad flour. Slices were removed at the end of incubation period and the supernatant removed for scintillation counting. The supernatant fractions were placed in scintillation vials containing NEN Formula 989 for a minimum of 12 hrs before being counted in a Beckman LS6000 scintillation counter. Results were normalized to the dpm counts of respective controls.

LDH Assays

Cortical slices were prepared as described above in the glutamate release experiments and placed in tissue culture wells containing Krebs-Heinsleight buffer supplemented with 0.0004% $H_2O_2$ and 1 mg/mL glucose. Extensive previous studies have demonstrated that this medium supports cellular activity for prolonged periods (Van Huizen et al., 1989; Shaw et al., 1996). (Note that hydrogen peroxide, added as the source of molecular oxygen, was not deleterious at this low concentration (see Van Huizen et al., 1989). In our preliminary experiments, hydrogen peroxide did not affect LDH release up to a 1 mM concentration (0.0034%). All slices were washed twice with buffer for 20 min each at room temperature before incubation in media containing the test compounds for 1 hr at 37° C. Test compounds included MSO, NMDA, kainate, different concentrations of cycad extract or different fractions or concentrations of isolated BSSG. MSO, NMDA, and cycad/BSSG were each tested alone or in combination with AP5, and compared to control slices maintained in buffer alone. For additional comparison and to establish the limits of the method, some slices were freeze-thawed to kill all the cells. Alternatively, some slices were incubated in buffer containing 1.2 mM $Mg^{2+}$ in order to diminish spontaneous neural activity. At the end of the 1 hr incubation period, 3 samples (100 µl of buffer, each sample) were taken from each well. LDH assays were performed on these samples using a LDH diagnostic kit (Sigma) following the manufacturer's protocol with some modifications. In brief, 0.5 ml of pyruvate solution was mixed with 0.5 mg pre-weighed NADH. 100 µl of slice medium (free of slices) was added to the mixture and incubated for 30 min at 37° C. 0.5 ml of Sigma coloring reagent (2,4-dinitrophenylhydrazine in HCl, 2 mg/ml) was added to develop the color and the mixture was incubated for 20 min at room temperature. 5 ml of 0.4 N NaOH were added to each tube. After 5 min, optical density was read at 440 nm. Standard curves were prepared for each assay using different concentrations of pyruvate solution (0-960 units). LDH activity (in International Units) was calculated from the standard curve and normalized by total protein content of each slice as determined by the Lowry protein assay (Peterson, 1979). One International Unit represents the amount of enzyme required to convert 1 µmol of substrate/minute at room temperature.

In Situ Labeling of DNA Fragmentation/Apoptosis

Terminal deoxynucleotidyl transferase (TdT) mediated dUTP-digoxigenin (DIG) nickend labeling (TUNEL) was carried out using an Intergen ApopTag Plus peroxidase kit using the manufacturer's protocol adapted from Gavrieli et al. (1992) with some modifications. More specific antibody labels for apoptosis, eg. caspase 3 also showed cell death in the same regions. Briefly, 20 µM thick coronal sections were cut on a cryostat then fixed in 1% paraformaldehyde at room temperature for 2 days. The endogenous peroxidase was quenched by 3% hydrogen peroxide in phosphate buffered solution (PBS). After rinsing with PBS, the sections were then exposed to 11 µL/cm$^2$ working strength of TdT enzyme for 1 hr at 37° C. After washing in PBS, 15||L/cm$^2$ of anti-digoxigenin-peroxidase was applied for 30 min in a humidified chamber at room temperature. Colour was developed by adding 125 µl DAB substrate working solution for 6 min. Slides were counter-stained with methyl green for 25 minutes at room temperature. Positive apoptosis controls were generated by pre-incubating sections with DNAase (Sigma). These methods have been successfully used to indicate apoptotic neurons when used in other preparations (Simpson et al., 2000).

Data for LDH and glutamate release experiments were analyzed for significance by one way ANOVA using Dunnett's and Bonferroni's post tests with GraphPad Prism™.

Tissue Culture Studies of BSSG Toxicity

Figure 5:
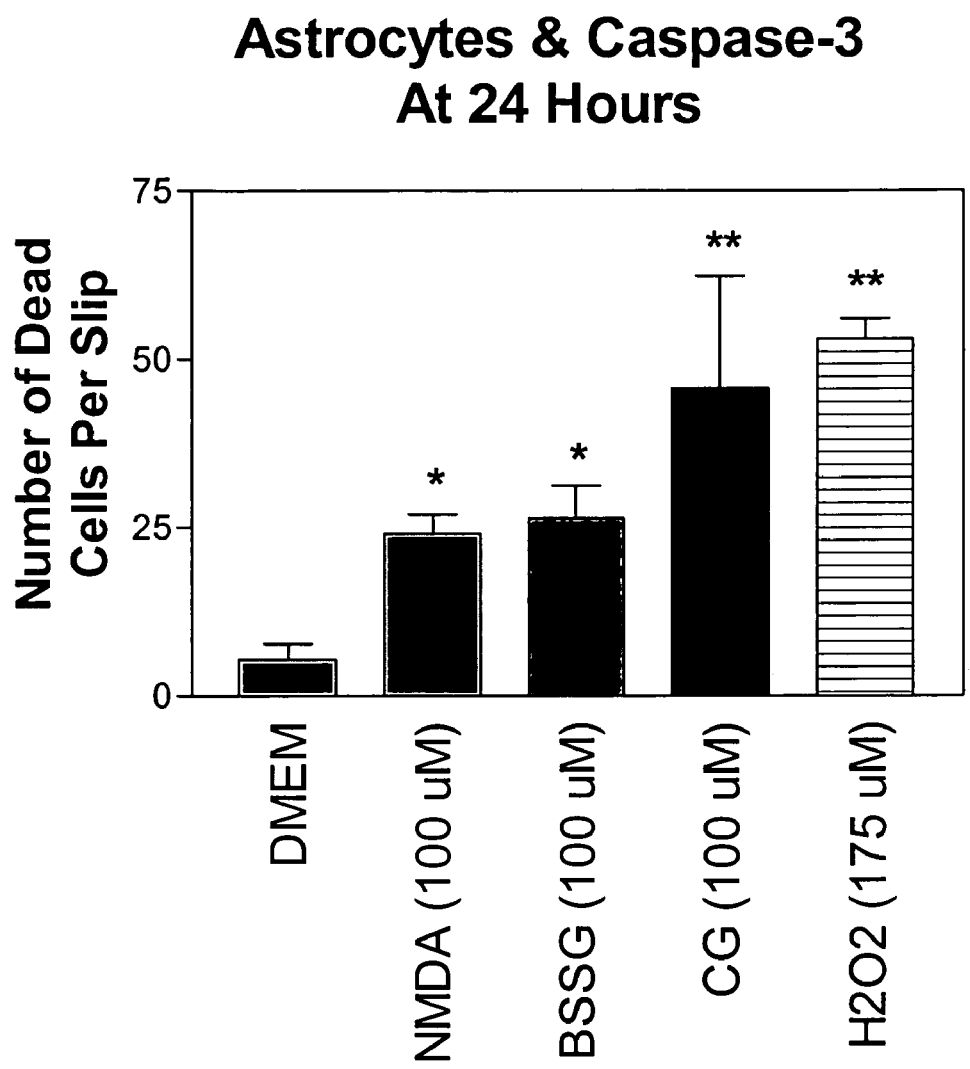
FIG. 5: Caspase-3 labeling of human cortical astrocytes in tissue culture. Fetal human telencephalic astrocytes were grown to confluency and then exposed to NMDA, BSSG, cholesterol glucoside (CG), or hydrogen peroxide ($H_2O_2$) for various periods. The peak of caspase-3 positive labeling was seen at 24 hrs. after exposure to the various compounds. Note significant caspase-3 positive labeling in all experimental conditions vs. control (DMEM), including for the sterol glucosides BSSG and CG. At longer time points, the overall numbers of cells in these conditions declined.
Figure 6:
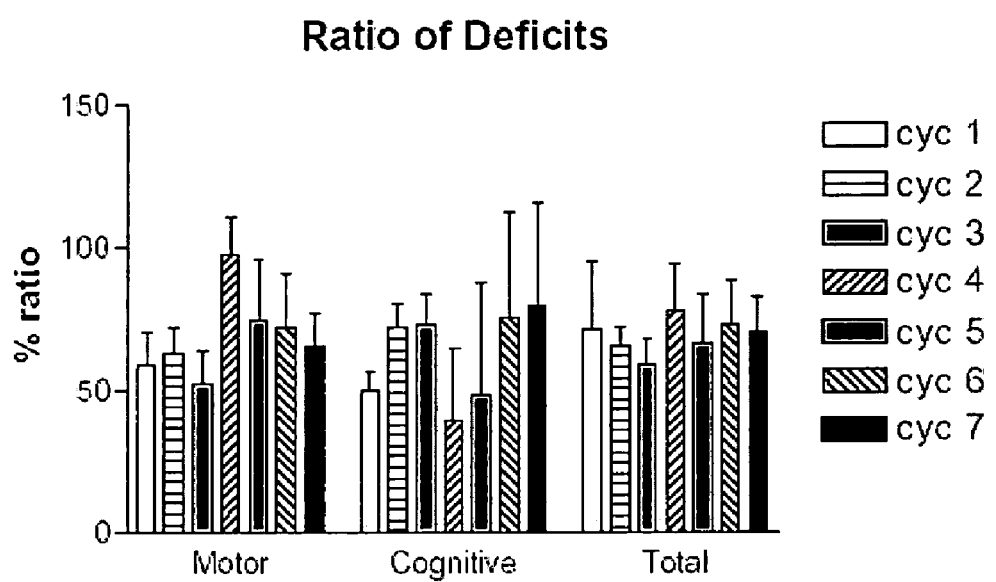
FIG. 6: Cumulative motor and cognitive deficits of seven cycad-fed animals (cyc 1 through cyc 7). Averages of the values recorded for each of the cycad animals on each of the behavioural tests described were expressed as a percentage in relation to the cumulative control values. Values were computed for motor, cognitive, or combined motor and cognitive functions as follows: Control values for any measure were averaged across all control animals and set to 100%. For each cycad animal, the individual response for each separate measure was described as % response/100; total cumulative response for cycad mouse is the sum average of all such separate measures/100. Left: Motor deficits. Centre: Cognitive deficits. Right: Combined motor and cognitive deficits. S.E.M. indicates variance across individual behavioural measures in each of the cycad-fed mice.

We have raised cortical astrocytes on coverslips in culture, exposing them to kainic acid, BSSH, or cholesterol glucoside. Cell loss was measured directly by cell density measurements; apoptosis was measured by staining cells for caspase-3 labeling. Each of these compounds generated a time-dependent apoptotic cell loss. These data are shown in FIG. 5.

Results

MSO and Cycad Mechanisms of Action in CNS

MSO, crude cycad extract, and BSSG isolated from cycad seed flour were tested for neural action and neuro-excitotoxicity in a series of bioassays. FIG. 1a shows the neural response to MSO measured as field potential in the cortical wedge preparation from adult rat. Bath application of MSO led to a relatively rapid depolarizing field potentials over a range of concentrations beginning at approx. 50 μM. The responses to glutamate receptor agonists NMDA and AMPA are also shown in the traces of FIG. 1a for comparison. MSO responses, like those of NMDA, could be blocked by the co-application of NMDA receptor antagonists AP5, kynurenate, or MK 801 (the latter not shown here). MSO responses were not blocked by application of AMPA antagonists NBQX or other AMPA antagonists. FIG. 1b shows LDH assays for rat cortical slices following exposure to MSO and other excitotoxins. Both NMDA and MSO increased cell death as measured by LDH release, and both treatments were blocked by the addition of AP5.

Figure 2:
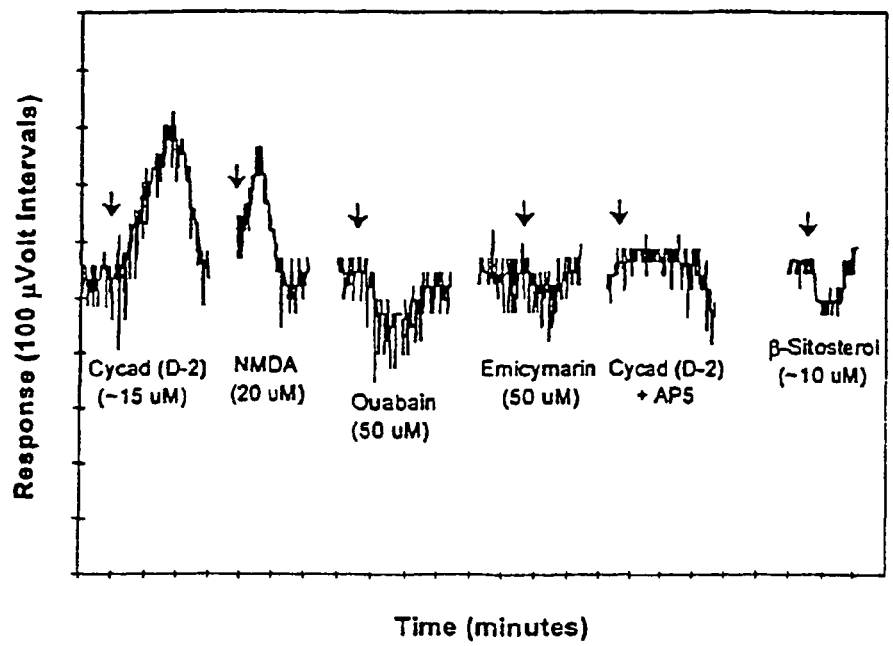
FIG. 2. Actions of isolated BSSG fractions on rat cortical slices. A. Field potential recording of isolated cycad sterol glucoside fraction D-2 (15 µM) compared to NMDA (20 µM), other plant sterol glucosides (ouabain or emicymarin, 50 µM), the β-sitosterol aglycone (10 µM), or D-2 plus AP5 (10 µM). Arrows indicate onset of drug application. B. LDH release following exposure to the same BSSG D-2 fraction (75 µM) compared to NMDA (50 µM), the sitosterol aglycone, β-SS (75 µM); various compounds in the presence of AP5 (20 µM). The action of cholesterol glucoside was qualitatively similar to β-sitosterol-β-D-glucoside (not shown). Statistics as in FIG. 1.
Figure 2:
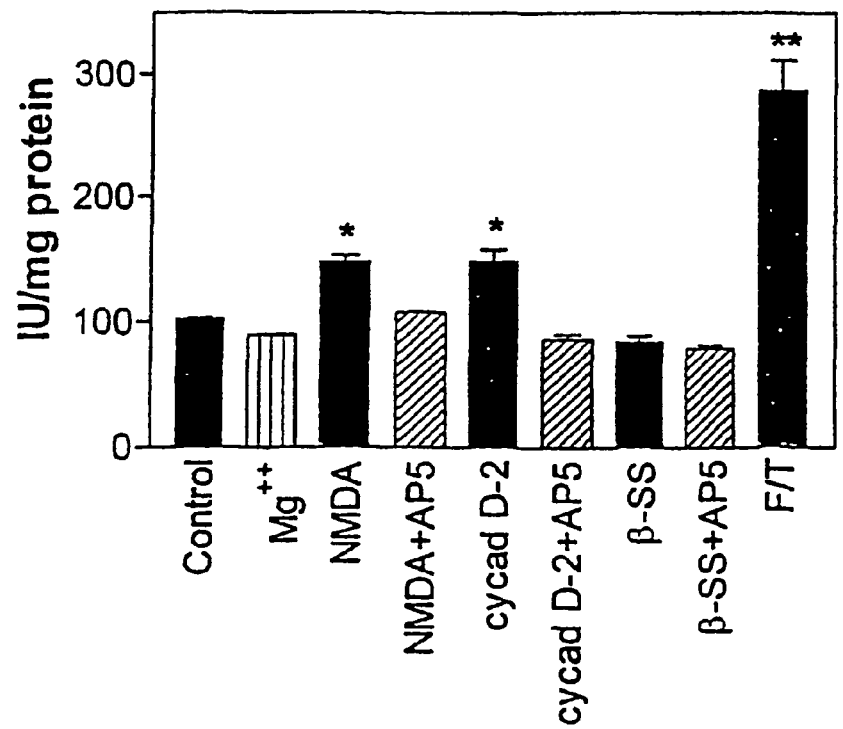

The actions of cycad flour extracts on the cortical wedge preparation are shown in FIG. 2. Cycad extracts gave depolarizing field potentials that could be blocked by MK801 (FIG. 2a) or AP5 (data not shown), but not NBQX (data not shown). LDH assays confirmed that cycad extract β-sitosterol-β-D-glucoside fractions gave increased LDH release that could induce cell death, an effect that was blocked by AP5 (FIG. 2b). Assays were also performed for comparison using other plant sterol glucosides (ouabain and emicymarin), and for synthetic cholesterol glucoside. The β-sitosterol agylcone and cholesterol were screened for comparison to the glucosides. Ouabain and emicymarin gave small hyperpolarizing responses and gave little LDH release (not shown). The aglycone sterols were without effect. The action of cholesterol glucoside was qualitatively similar to β-sitosterol-β-D-glucoside (not shown).

Figure 3A:
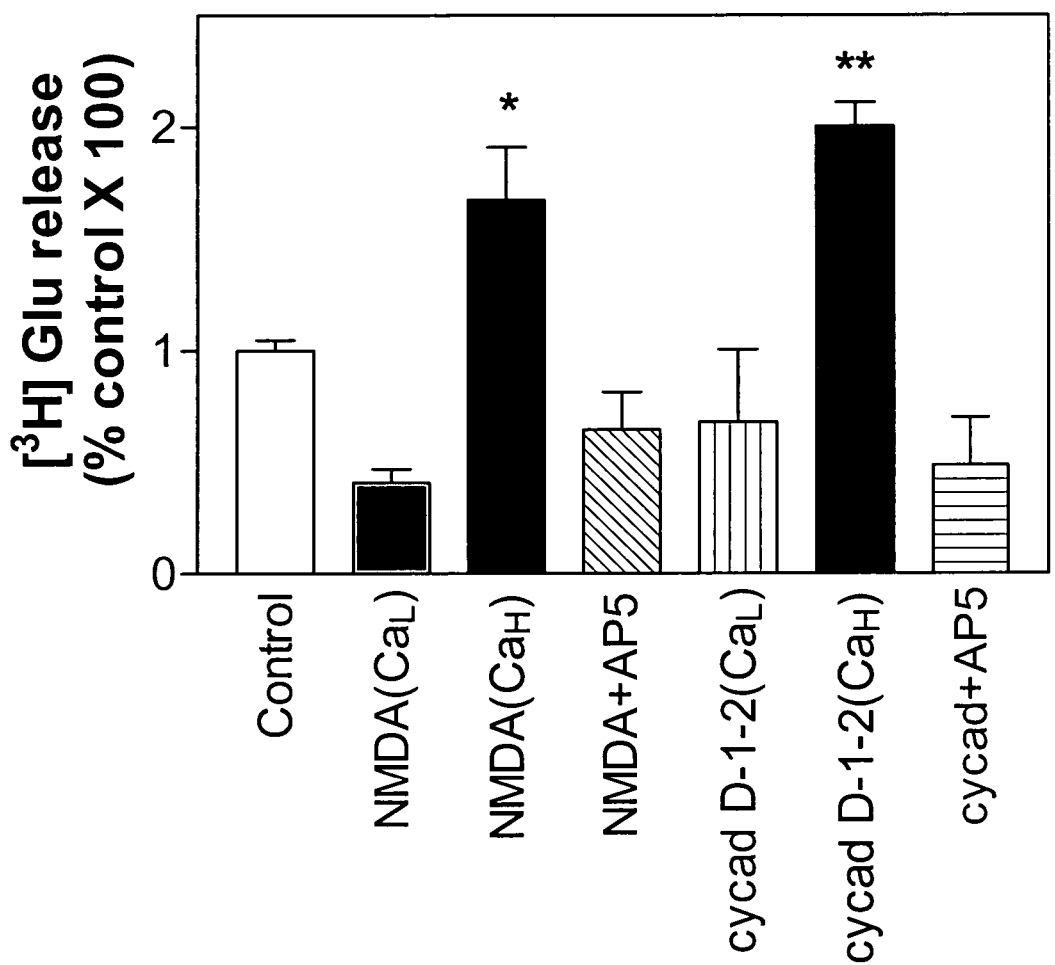
FIG. 3: [$^3$H]-glutamate release in rat cortical slices. A. [$^3$H]-glutamate release with isolated BSSG D-1-2 fraction (25 µM) compared to NMDA (50 µM) with or without AP5 (20 µM). For this experiment, calcium concentration was either 0 (L) or 2 mM (H). Note the calcium dependence for both NMDA and BSSG. B. [$^3$H]-glutamate release by D-2 BSSG fraction. Concentrations as in B.
Figure 3B:
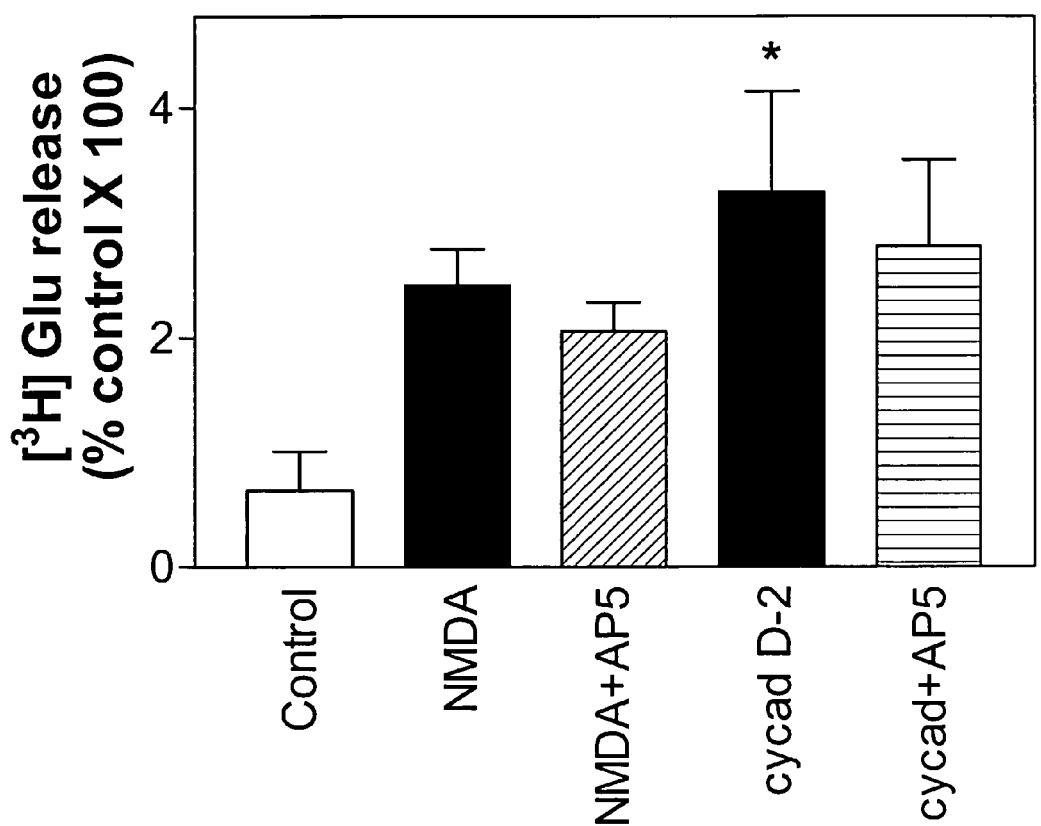

FIG. 3 shows results from the cortical wedge preparation (FIG. 3a) and in LDH assays (FIG. 3b) using isolated BSSG. The isolated BSSG fractions gave similar field potential responses that were blocked by NMDA antagonists. Cell death in LDH assays was also blocked by NMDA antagonists.

Figure 4A:
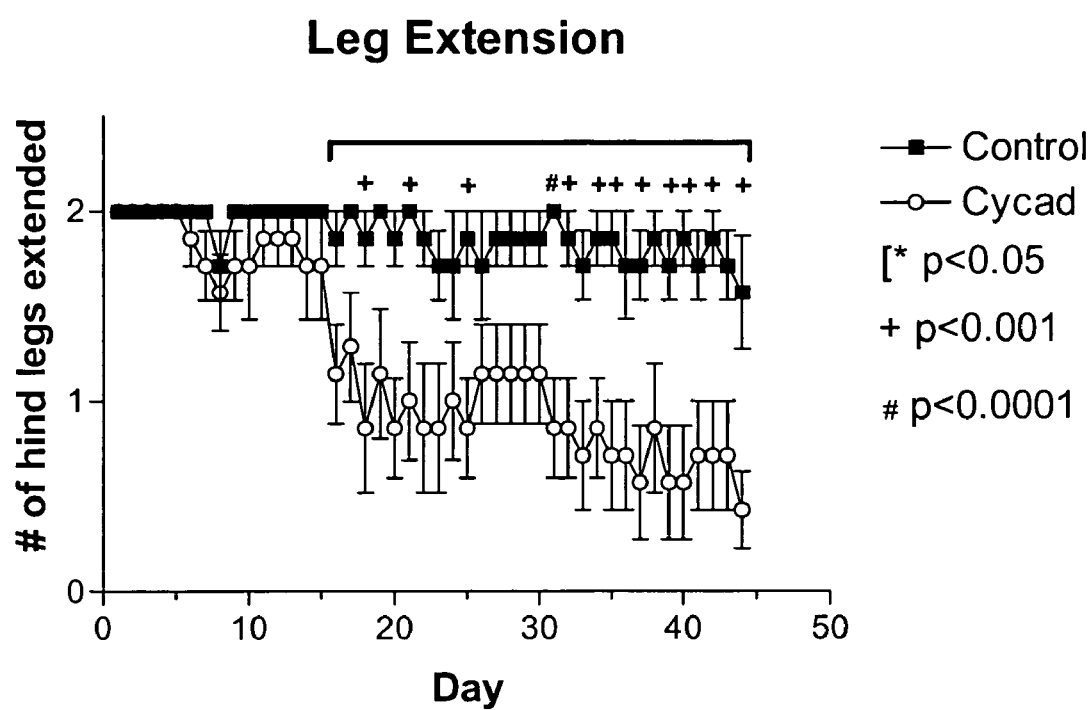
FIG. 4: Behavioral test results in the mouse model of neurodegenerative disease. A. Leg extension: the mouse is held by its tail, and in a normal mouse, both of its legs flex out (a score of 2 is recorded). If one or both of the legs do not flex out a score of 1 or 0 is given accordingly. B. Gait Length: the mouse walks through a tunnel with paint on its backpaws. Distance between subsequent paw prints is recorded as the gait length (stride length). C. Rotarod: the mouse is placed in a rotating cylinder, at increasing speeds. The time to fall of the cylinder and number of spins (rotations with out falling off) are recorded. D. Wire Hang: the mouse is placed up side down on a wire mesh and time to fall into a padded box is recorded. E. Water Maze: the mouse is placed in a small swimming pool of water and swims to find a hidden platform located near the middle of the pool. Time to find the platform and percentage of time in each quadrant of the pool is recorded. F. Radial Arm Maze: the mouse is placed in a 8 arm maze, in which 4 of the arms are baited with food. Errors are recorded as entries into unbaited tubes and re-entry in to tubes already visited.
Figure 4B:
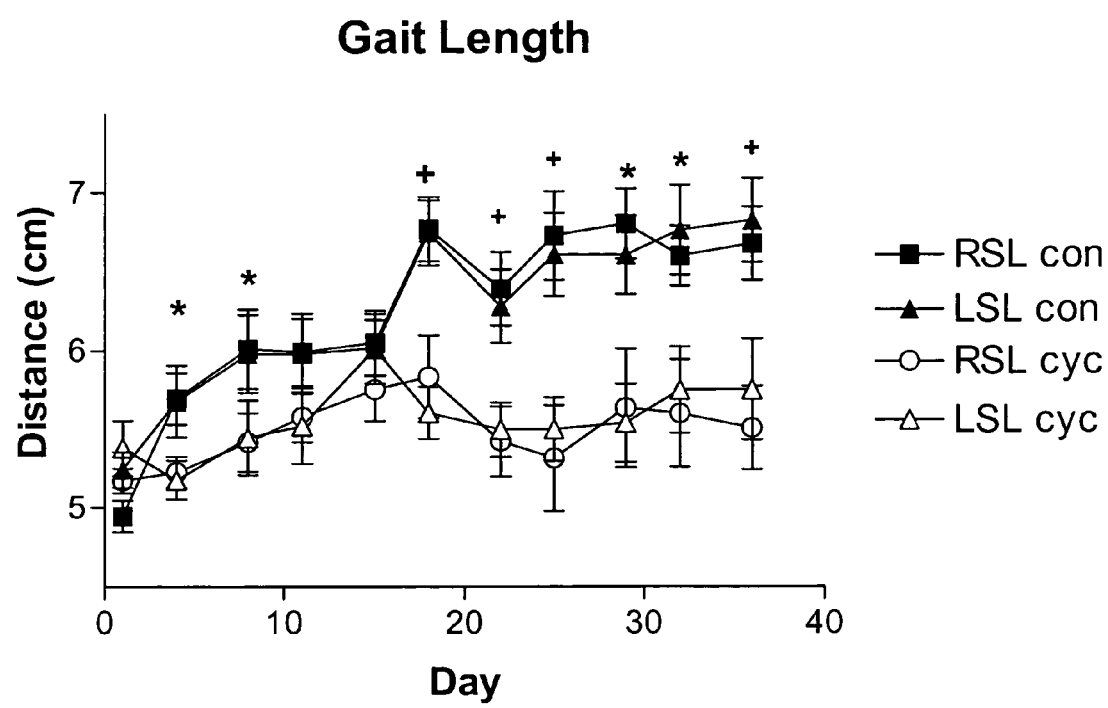
Figure 4C:
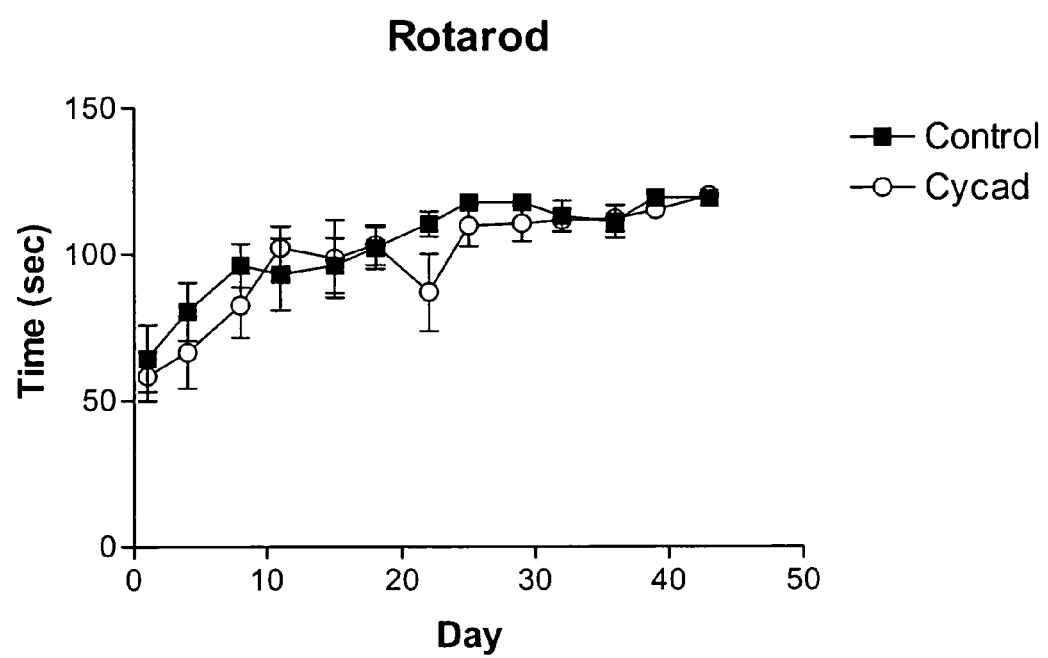
Figure 4D:
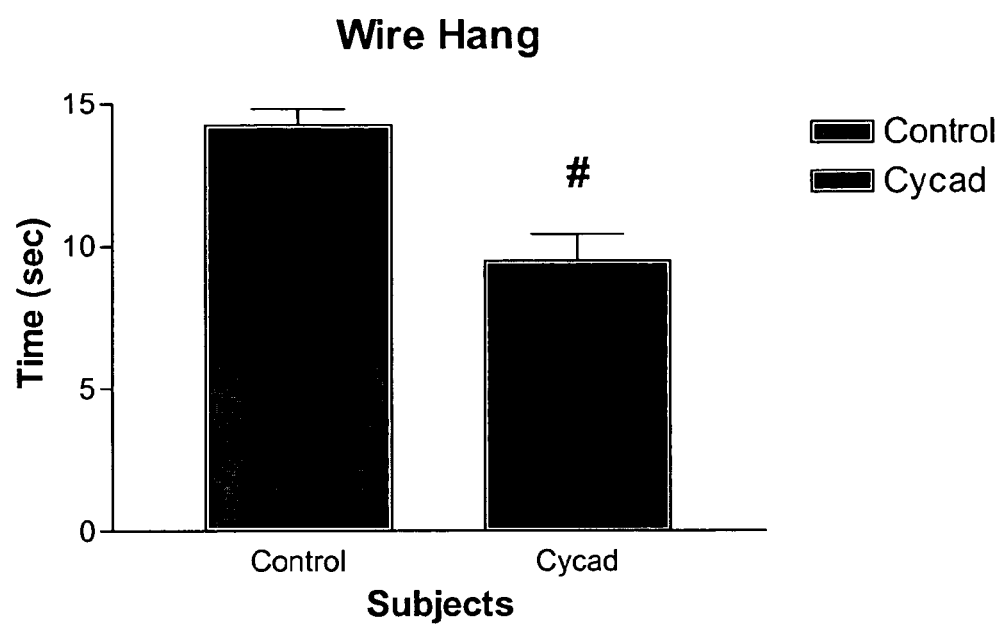
Figure 4E:
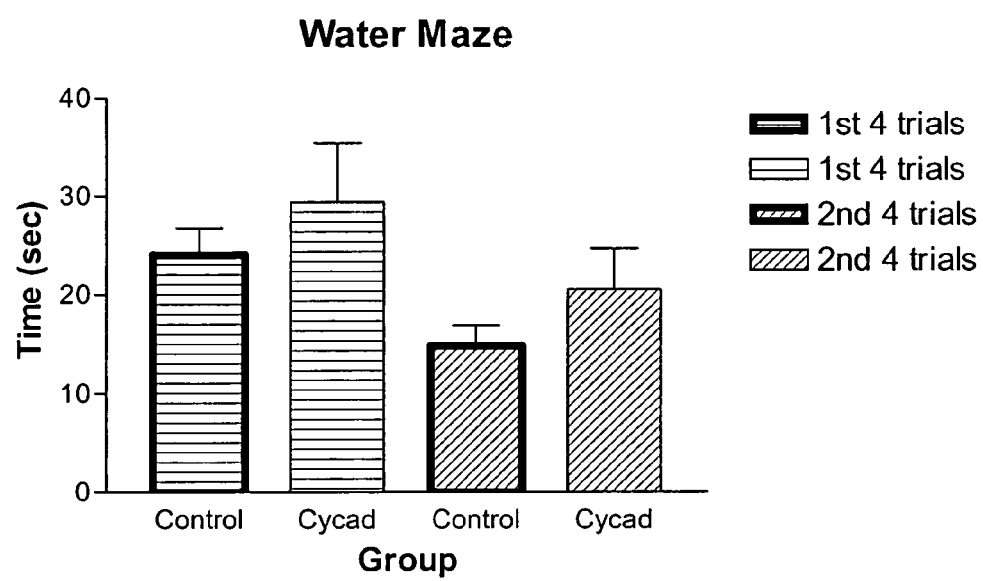
Figure 4F:
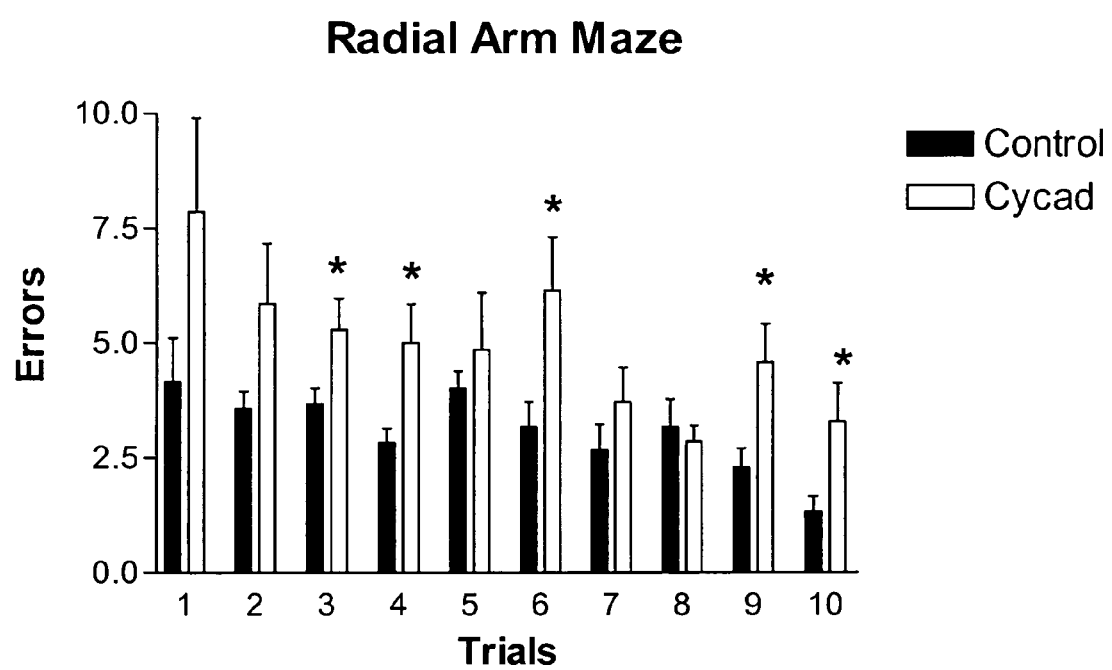

To test whether the actions of MSO and BSSG might act indirectly by releasing glutamate from intracellular compartments, we examined radiolabeled glutamate release from rat cortical slices. Preloaded [$^3$H]-glutamate release was significantly increased in the presence of MSO and BSSG fractions D-1-2 and D-2 (FIGS. 4abc) in a calcium dependent manner, and these effects could be blocked by AP5.

Cycad-fed animals showed significant and progressive deficits in both motor and cognitive function. Post-sacrifice histological examinations of the brains of cycad-fed animals revealed the presence of significant levels of apoptosis in hippocampal formation, cortex, and spinal cord compared to control mice. Rats fed MSO also showed evidence of apoptosis in CNS.

Synthesis of β-sitosterol-β-D-glucoside and Related Analogues.

The above experiments have demonstrated in vitro and in vivo neurotoxicity of cycad and have suggested that the toxic component in cycad is β-sitosterol-β-D-glucoside and related sterol glucosides. To test the hypothesis that β-sitosterol-β-D-glucoside is the active toxin requires either more of this compound extracted from cycad or the synthesis of the molecule de novo. As cycad is limited in supply, not to mention tedious to process, we have attempted to provide a synthetic pathway to acquire sufficient β-sitosterol-β-D-glucoside for future experiments. We have now accomplished this using the high yield methods set out below (provided by Drs. D. E. Williams and L. Lermer, UBC).

a. Preparation of D-glucose-pentaacetate

Glucose (20 g, 0.111 mols) and NaOAC (9.10 g, 0.111 mols) is added to a dry 1 L RBF under $N_2$. Acetic anhydride (125.7 ml, 1.332 mol, 12 eq) is added using a syringe. The solution is rapidly stirred and then warmed using a Bunsen burner until the solution becomes clear and colorless. The solution is allowed to cool to room temperature, forming a white precipitate. The solution is stirred for 2 hrs, taken up in EtOAc, washed with $H_2O$ 3×, 5% $NaHCO_3$ 3×, and 1× with brine. The organic layer is dried with $MgSO_4$, filtered and concentrated under reduced pressure, to afford D-glucose-pentaacetate, a white powder. The powder is re-crystallized in EthOH (approx. 400 ml) to afford 35.96 g of a white powder. The re-crystallized D-glucose-pentaacetate gives 42.02 g (65% yield). The mother liquor is concentrated and re-crystallized to afford a second crop of 6.60 g of D-glucose-pentaacetate as a white powder. The remaining mother liquor is concentrated to afford 18.82 grams of a white solid. An over all yield of 92.5% is obtained.

b. Preparation of 2,3,4,6-Tetra-O-acetyl-D-glucopyranose

Hydrazine acetate 5.1 g (55.39 mmol, 1.20 eq) is placed in a dry 500 ml RBF under nitrogen. Dry DMF (dried over CaSO4 and distilled at 5 mmHg) is added to the flask using a syringe. D-glucose-pentaacetate 17.96 g (46.00 mmol) is placed in a dry 250 ml RBF under nitrogen and dissolved in 100 ml dry DMF. The D-glucose-pentaacetate is added to the reaction flask via a cannula. After the addition of D-glucose-pentaacetate, the solution has a slightly yellow colour. Solid hydrazine remained suspended. After 3 hrs the suspension has dissolved and the solution remains clear pale yellow in colour. The solution is taken up in EtOAc, washed 3× with $H_2O$ and 1× with brine, dried over $MgSO_4$, filtered and concentrated under reduced pressure. 2,3,4,6-Tetra-O-acetyl-D-glucopyranose as clear colourless viscous oil is obtained. This oil is used without further purification in the next step.

c. Preparation of 2,3,4,6-Tetra-o-acetyl-α-D-glucosyl trichloroacetimidate

The viscous 2,3,4,6-Tetra-O-acetyl-D-glucopyranose oil is dissolved in dry $CH_2Cl_2$ 150 ml in a 500 ml RBF under nitrogen and cooled to −40° C. (cooling bath of $CH_3CN/CO_2$). $Cl_3CCN$ 46.11 ml (459.9 mmol, 10 eq) is added to the reaction flask drop wise using a syringe, followed by the addition of DBU (0.68 ml, 0.1 eq). After two hrs the solution is allowed to warm to room temperature. The solvent is removed under reduce pressure and the oil is loaded using a minimum of $CH_2Cl_2$ on a 8 cm diameter silica column. The column is eluted with 3:1 pet. ether:EtOAC followed by 2:1 pet.Ether: EtOAc. Three fractions are collected. The first fraction RF=0.63 contains 16.394 g of 2,3,4,6-Tetra-o-acetyl-α-D-glucosyl trichloroacetimidate (α-TAG-I) as a viscous oil. A second oil fraction is collected containing a mixture of α-TAG-I and small impurity of β-TAG-I 1.644 grams and a third fraction containing a 4.060 grams of β-TAG-I as a white powder. A 71% yield of 2,3,4,6-Tetra-o-acetyl-α-D-glucosyl trichloroacetimidate is obtained and a total overall yield of 87% is achieved.

d. Coupling—preparation of 2,3,4,6-Tetra-o-acetyl-β-D-glucosyl-β-sitosterol 2,3,4,6-Tetra-o-acetyl-α-D-glucosyl trichloroacetimidate (α-TAG-I) (1.771 g, 0.54 mmol, 1.5 eq) is pumped on over night and dissolved in dry $CH_2Cl_2$. The solvent is then removed under low pressure. Dry α-TAG-I in a 10 ml flask is re-dissolved in 5 ml of $CH_2Cl_2$. The α-TAG-I is transferred into the 25 ml RBF reaction flask containing activated 3 Å molecular sieves via a cannula. The solution is stirred for 1 hr over the sieves to take up any residual water. β-sitosterol (0.0994 g, 0.24 mmol) is dissolved in 5 m 1 dry $CH_2Cl_2$ and transferred in the reaction flask via a cannula. The flask containing sitosterol is rinsed with 1 ml $CH_2Cl_2$. The rinse is added to the reaction flask. The reaction is cooled to −23° C. (cooling bath of $CCl_4/CO_2$) and some precipitation occurs. A syringe is used to inject a 0.99 ml volume of a stock solution of 0.1 ml $BF_3.Et_2O$ in 8 ml $CH_2Cl_2$ drop wise over 20 min to the reaction flask. The solution remains clear and colorless. After 2 hrs no precipitation remains in the reaction flask. After 4 hours a fine white precipitate is observed. The reaction is completed by TLC using (9:1 $CHCl_3$:MeOH). A second addition of TAG-I (0.1180 g, 0.239 mmol, 1 eq) dissolved in 5 ml $CH_2Cl_2$ is added drop wise to the flask. After 1 hr, no starting material is present. The solvent is evaporated under reduced pressure and the oil is loaded on a silica column. The column is eluted with 10:1 pet. ether:EtOAc (10 collection tubes) followed by 3:1 pet. ether:EtOAc (15:tube) followed by 1:1 3:1 pet. ether:EtOAc. Two fractions are obtained. The first fraction contains 0.0219 g-β-sitosteryl acetate. The second fraction contains 0.1392 g (78%) of 2,3,4,6-Tetra-o-acetyl-β-D-glucosyl-β-sitosterol. (Note: The sterol and the product have very similar RF's using Pet. Ether:EthOAc solvent to elute. The reaction may be followed using a 9:1 solution of $CHCl_3$:MeOH to elute the TLCs).

e. Deacetylation—preparation of β-Sitosteryl-β-D-glucopyranoside

The 2,3,4,6-Tetra-o-acetyl-β-D-glucosyl-β-sitosterol 0.1392 g is dissolved in 80 ml warm MeOH. The solution is allowed to cool back to room temperature. Some precipitation is observed. $Et_3N$ (12 ml) is added followed by 2 ml of $H_2O$. After three hrs the precipitate has re-dissolved, and the clear, colorless solution is stirred overnight. A fine white precipitate is observed in the reaction flask the next morning. TLC using 15% MeOH/$CHCl_3$ indicates that the reaction is complete. The solvent is removed under reduced pressure to afford a white solid. The solid is re-dissolved in a minimum amount of 15% MeOH/$CHCl_3$ The solution is loaded on a silica column eluted with 15% MeOH/$CHCl_3$. A single white powder 0.1079 g (100% yield) is obtained. These methods result in an overall yield of 78% for the combination of the coupling and deacetylation reactions. The white solid is re-crystallized in Ethanol to afford 0.0452 g (42%) of a white powder. The mother liquor is concentrated and a second crop is obtained of 0.0165 g (15%) of a white powder. The mother liquor is concentrated and the solid is re-crystallized using a $H_2O$/MeOH mixed solvent system to afford 0.0044 g (4%). The remaining mother liquor is concentrated to afford 0.0180 g (17%). The overall yield from the 0.0994 g of sitosterol is 0.0661 g (48%) of re-crystallized β-sitosteryl-β-D-glucopyranoside and 0.018 g (13%) of remaining non-recrystallized β-sitosteryl-β-D-glucopyranoside product. Note that the 0.0219 g of β-sitosteryl acetate from the coupling reaction can be recycled back to sitosterol and then carried through to the desired product in order to increase yields.

Wedge recording and LDH assays using synthetic β-sitosterol-β-D-glucoside created by these methods have been shown qualitative similarity between the synthetic and natural D-2 fractions

REFERENCES

Bains, J. S. and Shaw, C. A. Neurodegenerative disorders in humans: the role of glutathione in oxidative stress-mediated neuronal death. Brain Res. Rev. 1997, 335-358.

Bindokas, V. P., Lee, C. C., Colmers, W. F., and Miller, R. J. Changes in mitochondrial function resulting from synaptic activity in rat hippocampal slice. J. Neurosci. 1998, 18: 4570-4587.

Campbell, P. N., Work, T. S., and Mellanby, E. Isolation of crystalline toxic factor from agenized wheat flour. Nature. 1950, 165: 345-346.

Choi, D. W., Calcium: still center-stage in hypoxic-ischemic neuronal death. Trends Neurosci. 1995, 18: 58-60.

Cooper, A. J. L. Role of astrocytes in maintaining cerebral glutathione homeostasis and in protecting the brain against xenobiotics and oxidative stress. In: Glutathione in the Nervous System, Shaw, C. A. (ed.), Taylor and Francis Pub., Washington, 1998, pp. 91-116.

Earnshaw, W. C. Apoptosis: lessons from in vitro systems. Trends Cell Biol. 1995, 5: 217-220.

Ellis, R. E., Yuan, J., and Horvitz, H. R. Mechanisms and functions of cell death. Ann. Rev. Cell Biol. 1991, 7: 663-698.

Evans, P. H. Free radicals in brain metabolism and pathology. Br. Med. Bull. 1993, 49: 577-587.

Gavreili, Y., Sherman, Y., and Ben-Sasson, S. A. Identification of programmed cell death via specific labeling of nuclear DNA fragmentation. J. Cell Biol. 1992, 119: 493-501.

Higuchi, Y. and Matsukawa, S. Glutathione depletion induces giant DNA and high molecular weight DNA fragmentation associated with apoptosis through lipid peroxidation and protein kinase C activation in C6 glioma cells. Arch. Biochem. Biophys. 1999, 363: 33-42.

Hockenbery, D. M., Oltvai, Z. N., Yin, X.-M., Millian, C. L., and Korsmeyer, S. J. Bcl-2 functions in an antioxidant pathway to prevent apoptosis. Cell. 1993, 75: 241-251.

Janaky, R., Ogita, K., Pasqualotto, B. A., Bains, J. S., Oja, S. S., Yoneda, Y., and Shaw, C. A. Glutathione and signal transduction in the mammalian CNS. J. Neurochem. 1999, 73: 889-902.

Katayama, R., Cheun, M. K., Gorman, L., Tamura, T., and Becker, D. P. Increase in extracellular glutamate and associated massive ionic fluxes following concussive brain injury. Soc. Neurosci. Abstr. 1988, 14: 1154.

Khabazian, I., Pelech, S. L., Williams, D. E., Andersen, R. J., Craig, U.-K., Krieger, C., and Shaw, C. A. Mechanisms of action of sitosterol glucoside in mammalian CNS. Soc. Neurosci. Abstr. 2000, 26: 2074.

Kurland, L. T. Amyotrophic lateral sclerosis and Parkinson's disease complex on Guam linked to an environmental toxin. Trends Neurosci. 1988, 11: 51-53.

Meldrum, B. and Garthwaite, J. Excitatory amino acid neurotoxicity and neurodegenerative disease. Trends Pharmacol. Sci. 1990, 11: 379-386.

Meister, A. and Tate, S. S. Glutathione and related gamma glutamyl compounds: biosynthesis and utilization. Annu. Rev. Biochem. 1976, 45: 559-604.

Nagata, S. Apoptosis by death factor. Cell. 1997, 88: 355-365.

Newell, G. W., Erickson, T. C., Gilson, W. E., Gershoff, S. N., and Elvehjem, C. A. Role of "agenized" flour in the production of running fits. J. Am. Med Assoc. 1947, 135: 760-763.

Nicole, A., Santiard-Baron, D., Cellballos-Picot, I. Direct evidence for GSH as mediator of apoptosis in normal cell death. Biomed. Pharmacother. 1998, 52: 349-355.

Palmer, A. M. The activity of pentose phosphate pathway is increased in response to oxidative stress in Alzheimer's disease. J. Neural Trans. 1999, 106: 317-328.

Perl, T. M., Bedard, L., Kosatsky, T., Hockin, J. C., Todd, E. C. D., and Remis, R. S. An outbreak of toxic encephalopathy caused by eating muscles contaminated with domoic acid. N. Eng. J. Med. 1990, 322: 1775-1780.

Peterson, G. L. Review of the Folin phenol protein quantification method of Lowry, Rosebrough, Farr and Randall. Anal. Biochem. 1979, 83: 201-220.

Pow, D. V., Barnett, N. L., and Penfold, P. Are neuronal glutamate transporters relevant in retinal glutamate homeostatis? Neurochem Intl. 2000, 37: 191-198.

Rechcigl, M. Rates and kinetics of catalase synthesis and destruction in rats fed cycad and cycasin in vivo. Fed. Proc. 1964, 23: 1376-1377.

Rechcigl, M. and Laqueur, G. L. Carcinogen-mediated alteration of the rate of enzyme synthesis and degradation. Enzym. Biol. Clin. 1968, 9: 276-286.

Rothstein, J. D., Martin, L. J., Kuncl, R. W., Decreased glutamate transport by the brain and spinal cord in amyotrophic lateral sclerosis. N. Eng. J. Med. 1992, 326: 1464-1468.

Rothstein, J. D., Tsai, G., and Kuncl, R. W., Clawson, L., Comblath, D. R., Drachman, D. B., Pestronk, A., Staunch, B. L., and Coyle, J. T. Abnormal excitatory amino acid metabolism in amyotrophic lateral sclerosis. Ann. Neurol. 1990, 28: 18-25.

Rothstein, J. D., Van Kammen, M., Levey, A., Martin, L. J., and Kuncl, R. W. Selective loss of glial glutamate transporter GLT-1 in amyotrophic lateral sclerosis. Ann. Neurol. 1995, 38: 73-84.

Russel, R. L., Siedelak, S. L., Raina, A. K., Bautista, J. M., Smith, M. A., and Perry, G. Increased neuronal glucose-6-phosphate dehydrogenase and sulfhydryl levels indicate reductive compensation to oxidative stress in Alzheimer's disease. Arch. Biochem. Biophys. 1999, 370: 236-239.

Shaw, C. A. and Bains, J. S. Did consumption of flour treated by the agene process contribute to the incidence of neurological disease? Med. Hyp. 1998, 51: 477-481.

Shaw, C. A., Bains, J. S., Pasqualotto, B. A., Curry, K. Methionine sulfoximine shows excitotoxic actions in rat cortical slices. Can. J. Physiol. Pharmacol. 1999a, 77: 871-877.

Shaw, C. A., Bains, J. S., Williams, D. E., Andersen, R. J., Pasqualotto, B. A., Cheung, J., Tjandrawidjaja, M., Wilkinson, M., Janaky, R., Craig, U.-K. Identification of a novel excitotoxin from cycad seed: implications for neuronal disorders. Soc. Neurosci. Abstr. 1999b, 25: 1304.

Shaw, C. A., Pasqualotto, B. A., and Curry, K. Glutathione-induced sodium currents in neocortex. Neuroreport. 1996, 7: 1149-1152.

Shaw, P. J. and Ince, P. G. Glutamate, excitotoxicity and amyotrophic lateral sclerosis. J. Neurol. 1997, 244 (Suppl. 2): S3-S14.

Sies, H. (Ed.). Oxidative stress: Oxidants and Antioxidants, Academic Press, New York, 1991.

Simpson, R. J., Khabazian, I., Williams, D. E., Andersen, R. J., Craig, U., and Shaw, C. A. Apoptotic and non-apoptotic cell death following MSO and cycad treatments. Soc. Neurosci. Abstr. 2000, 26: 261.

Simonian, N. A. and Coyle, J. T. Oxidative stress in neurodegenerative diseases. Ann. Rev. Pharmacol. Toxicol. 1996, 36: 83-106.

Triosh, O., Sen, C. K., Roy, S., Packer, L. Cellular and mitochondrial changes in glutamate-induced HT4 neuronal cell death. Neurosci. 2000, 97: 537-541.

Van Huizen, F., Shaw, C., Wilkinson, M., and Cynader, M. Characterization of muscarinic acetylcholine receptors in rat cerebral cortex slices with concomitant morphological and physiological assessment of tissue viability. Mol. Brain Res. 1989, 5: 59-69.

Verarucci, D., Verarucci, V., Vallese, A., Battila, L., Casado, A., De la Torre, R., and Lopez Fernandez, M. E. Free radicals: important cause of pathologies refer to ageing. Panmineva Medica. 1999, 41: 335-339.

Watanabe, M. Developmental regulation of ionotropic glutamate receptor gene expression and functional correlations. In: Receptor Dynamics in Neural Development, Shaw, C. A. (ed.), CRC Press, Boca Raton, 1996, pp. 73-89.

Wullner, U., Seyfried, J., Groscurth, P., Beimroth, S., Winter, S., Gleichmann, M., Heneke, M., Loschmann, P., Schutz, J. B., Weller, M., and Klockgether, T. Glutathione depletion and neuronal cell death: the role of reactive oxygen intermediates and mitochondrial function. Brain Res. 1999, 826: 53-62.

Zaman, K. and Ratan, R. R. Glutathione and the regulation of apoptosis in the nervous system. In:

Glutathione in the Nervous System, Shaw, C. A. (ed.), Taylor and Francis Pub., Washington, 1998, pp. 117-136.

Zeevalk, G. D. and Nicklaus, W. J. Mechanisms underlying initiation of excitotoxicity associated with metabolic inhibition. J. Pharm. Exp. Ther. 1990, 257: 870-878.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Given the overlap in the occurrence of particular sterols in plants, animals and other organisms, the present application refers to all such compounds collectively as sterols. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for examining neurodegeneration in a non-human mammal, the method comprising the step of:

administering a synthetic neurotoxic sterol glycoside to the mammal, wherein the neurotoxic sterol glycoside causes the neurodegeneration in the mammal, and wherein the neurodegeneration in the mammal is examined by observing behavioral abnormalities in the mammal or is examined post-mortem in a central nervous system tissue of the mammal wherein the neurotoxic sterol glycoside is selected from the group consisting of beta-sitosterol-beta-D-glucoside and cholesterol glucoside.

2. The method of claim 1, wherein a glycosidic bond in the sterol glycoside has been hydrolyzed prior to the administering step.

3. The method of claim 1 wherein the sterol glycoside has been treated with an enzyme that degrades the neurotoxic sterol glycoside.

4. The method of claim 1 wherein the neurological degeneration is identified by a behavioral test selected from the group consisting of a leg extension test, a gait length test, a rotarod test, a wire hang test, a water maze test, and a radial arm maze test.

5. The method of claim 1, wherein the sterol glycoside is cholesterol glucoside.

6. The method of claim 1, wherein the sterol glycoside is beta-sitosterol-beta-D-glucoside.

7. The method of claim 4, wherein the sterol glycoside is beta-sitosterol-beta-D-glucoside.

8. The method of claim 1, wherein the sterol glycoside is cholesterol glucoside, and wherein the cholesterol glucoside causes neuronal excitotoxicity.

9. The method of claim 6, wherein the beta-sitosterol-beta-D-glucoside is a compound of the formula 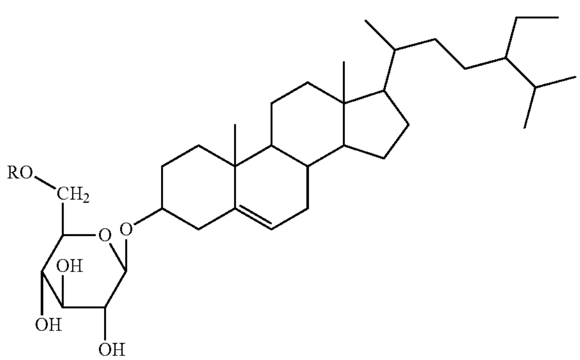 wherein R is hydrogen or $C_{15}H_{31}CO$.

10. The method of claim 7, wherein the beta-sitosterol-beta-D-glucoside is a compound of the formula 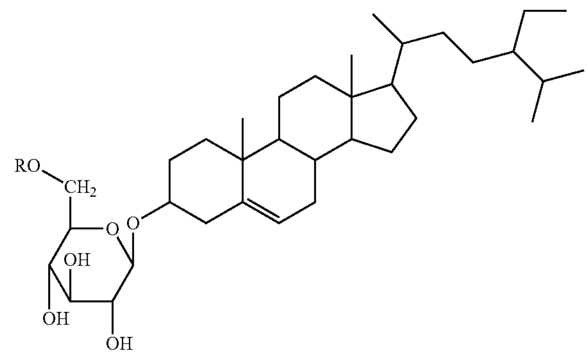 wherein R is hydrogen or $C_{15}H_{31}CO$.

11. The method of claim 3, wherein the enzyme that degrades the neurotoxic sterol glycoside is beta-d-glucosidase.

12. The method of claim 1, wherein the sterol glycoside is beta-sitosterol-beta-D-glucoside, and wherein the beta-sitosterol-beta-D-glucoside causes neuronal excitotoxicity.

13. The method of claim 1, wherein the neurological degeneration is at a site selected from the group consisting of the cortex, the hippocampus, the spinal cord, and the substantia nigra.

14. The method of claim 1, wherein the sterol glycoside causes a behavioral abnormality, and wherein the behavioral abnormality is an abnormality in motor function.

15. The method of claim 1, wherein the sterol glycoside causes a behavioral abnormality, and wherein the behavioral abnormality is an abnormality in cognitive function.

16. The method of claim 9, wherein the beta-sitosterol-beta-D-glucoside is non-acylated.

* * * * *